United States Patent [19]
Sioud

[11] Patent Number: 5,985,620
[45] Date of Patent: *Nov. 16, 1999

[54] TNF-α RIBOZYMES

[75] Inventor: Mouldy Sioud, Oslo, Norway

[73] Assignee: Gene Shears Pty. Limited, New South Wales, Australia

[ * ] Notice: This patent is subject to a terminal disclaimer.

[21] Appl. No.: 08/428,252

[22] PCT Filed: Nov. 3, 1993

[86] PCT No.: PCT/AU93/00567

§ 371 Date: Jun. 22, 1995

§ 102(e) Date: Jun. 22, 1995

[87] PCT Pub. No.: WO94/10301

PCT Pub. Date: May 11, 1994

Related U.S. Application Data

[63] Continuation-in-part of application No. 07/971,058, Nov. 3, 1992, abandoned.

[51] Int. Cl.$^6$ ............................ C12P 19/34; C07H 21/04; C12N 15/85; C12N 15/63
[52] U.S. Cl. ........................... 435/91.31; 435/6; 435/91.1; 435/91.3; 435/91.33; 435/320.1; 435/440; 435/455; 435/471; 435/325; 435/243; 514/44; 536/23.1; 536/23.2; 536/24.5
[58] Field of Search ............................. 435/6, 91.1, 91.3, 435/91.31, 91.33, 172.1, 172.3, 240.1, 240.2, 320.1, 455, 471, 325, 243; 514/44; 536/23.1, 23.2, 24.5

[56] References Cited

U.S. PATENT DOCUMENTS

| | | | |
|---|---|---|---|
| 4,666,848 | 5/1987 | Gelfand et al. | 435/252.33 |
| 5,107,065 | 4/1992 | Shewmaker et al. | 800/205 |
| 5,149,635 | 9/1992 | Gillies | 435/69.1 |
| 5,298,612 | 3/1994 | Jennings et al. | 536/23.2 |

FOREIGN PATENT DOCUMENTS

| | | |
|---|---|---|
| 8905852 | 6/1989 | WIPO . |
| 9207065 | 4/1992 | WIPO . |

OTHER PUBLICATIONS

Grosshans and Cech, (1991) "A hammerhead ribosome allows synthesis of a new form of the Tetrahymena ribozymes homogeneous in length with a 3' end blocked for transesterification." Nucleic Acid Research, 19(14):3875–3880.

Kisich, K.O. and Erickson, K.L., (1991) "Anti–tumor necrosis factor–a mRNA within mammalian cells." *Journal of Leukocyte Biologynd Cellular Biology,* Supplemental 2, p.70.

Cotten, Matt, (1990) "The in vivo application of ribozymes." *Elsevier Science Publishers Ltd.*, 8 (7): 174–178 (Exhibit 3).

Baralle, F.E. (1983) The Functional Significance of Leader and Trailer Sequences in Eukaryotic mRNAs. International Rev. of Cytology 81:71–106.

Beutler, B. and Cerami, A. (1989) The Biology of Cachetin/TNF–A Primary Mediator of the Host Response. Ann. Rev. Immunol. 7:625–655.

Elela, S.A. and Nazar, R.N. (1992) Extended Secondary Structure as a.

Basis of Increased RNA Stability in a thermophilic alga Cyanidium caldarium. Biochimica et Biophysica Acta. 130:339–342.

Haseloff, J. and Gerlach, W.L. (1988) Simple RNA Enzymes with New and Highly Specific Endoribonuclease Activities. Nature 334:585–591.

Hsu, Y.–P. and Schimmel, P. (1984) Yeast LEU1. J. Biol. Chem. 259(6):3714–3719.

Nielsen, D.A. and Shapiro, D.J. (1990) Insights into Hormonal Control of Messenger RNA Stability. Mol. Endo. 4(7):953–957.

Perreault, J. et al. (1990 Mixed deoxyribo–and ribo–oligonucleotides with catalytic activity. Nature 344:565–567.

Proudfoot, N.J. and Brownlee, G.G. (1976) 3' Non–coding Region Sequences in Eukaryotic Messenger RNA. Nature 263:211–214.

Ross, H.J. et al. (1991) Cytokine Messenger RNA Stability is Enhanced in Tumor Cells, Blood 77(8):1787–1795.

Rossi, J.J. et al. (1992) Ribozymes as Anti–HIV–1 Therapeutic Agents: Principles, Applications, and Problems. AIDS Research and Human Retroviruses 8(2):183–189.

Saini, K.S. et al. (1990) Molecular Events Regulating Messenger RNA.

Stability in Eukaryotes. Mol. and Cell. Biochem. 96:15–23; Shaw, G. and Kamen, R. (1986) A Conserved AU Sequence from the 3' .

Untranslated Region of GM–CSF mRNA Mediates Selective mRNA Degradation. Cell 46:659–667.

Sioud, M. and Drlica, K. (1991) Prevention of Human Immunodeficiency Virus Type I Integrase Expression in *Escherichia coli* by a Ribozyme.

Proc. Natl. Acad. Sci. U.S.A. 88:7303–7307; Sioud, M. et al. (1992) Preformed Ribozyme Destroys Tumor Necrosis.

Factor mRNA in Human Cells. J. Mol. Biol. 223:831–835; and Zaret, K.S. and Sherman, F. (1984) Mutationally Altered 3' Ends of.

Yeast CYC1 mRNA Affect Transcript Stability and Translational Efficiency. Mol. Biol. 176:107–135.

(List continued on next page.)

Primary Examiner—George C. Elliott
Assistant Examiner—Sean McGarry
Attorney, Agent, or Firm—John P. White; Cooper & Dunham LLP

[57] ABSTRACT

This invention describes compounds active against TNF-α mRNA. It further describes RNA molecules capable of conferring stability to RNA in vivo through an endogenous ribozyme binding protein(s). Possible mRNA molecules to be stabilized include ribozymes, antisense molecules and mRNA encoding polypeptides useful for protein production. The ribozymes and antisense molecules described herein are useful in mammals and plants, particularly suited for viral diseases. Methods of production and methods of use are also described.

24 Claims, 30 Drawing Sheets

OTHER PUBLICATIONS

Sioud, M "Interaction Between Tumour Necrosis Factor & Ribozyme and Cellular Proteins" *J of Molecular Biology*, vol. 242(5): 619–629, Oct. 1994.

Perriman et al "Manipulating Gene Expression by Ribozyme Technology" *Current Opinion in Biotechnology*, vol. 1: 86–91, 1990.

Rossi, J. "Controlled, Targeted, Intracellular Expression of Ribozymes: Progress and Problems" *TIBTECH* vol. 13: 301–306, 1995.

Stull et al, "Antigene, Ribozyme and Aptomer Nucleic Acid Drugs: Progress & Prospects". *Pharmaceutical Research* vol. 12 No.4: 465–483, 1995.

← 1.5 kB

← 0.5 kB

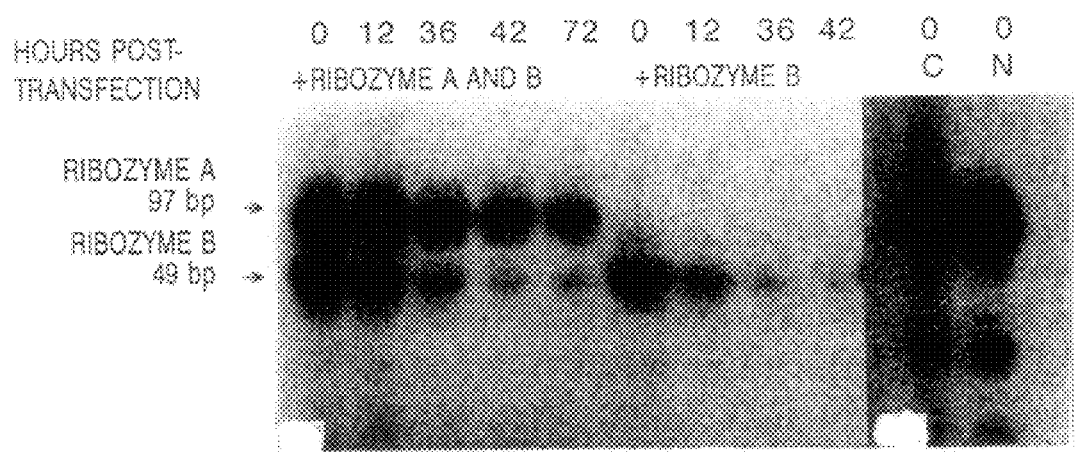

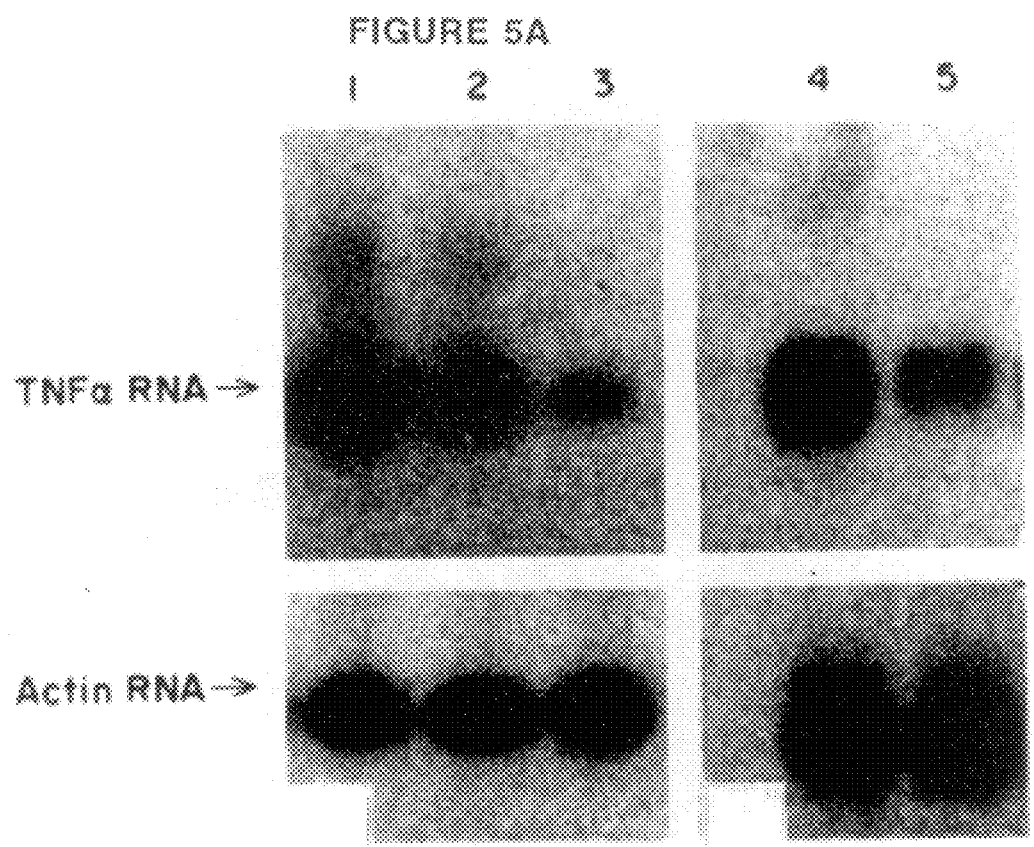

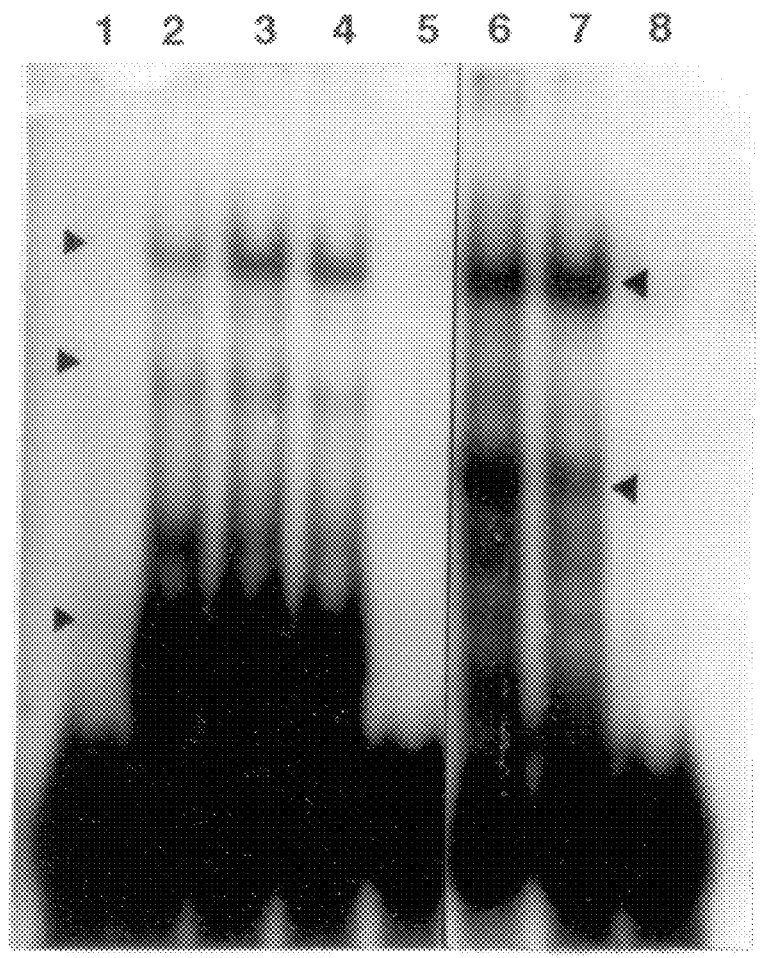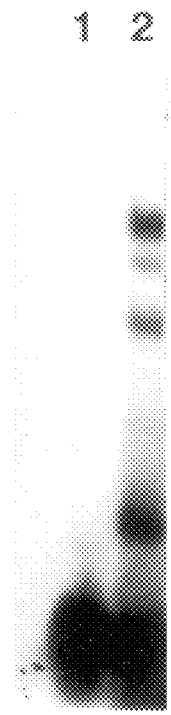
FIGURE 7B
FIGURE 7C

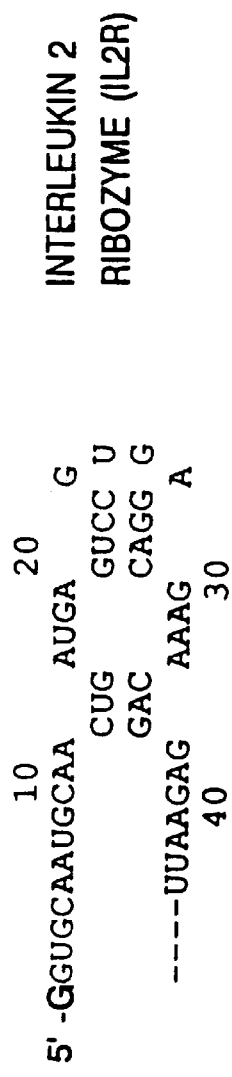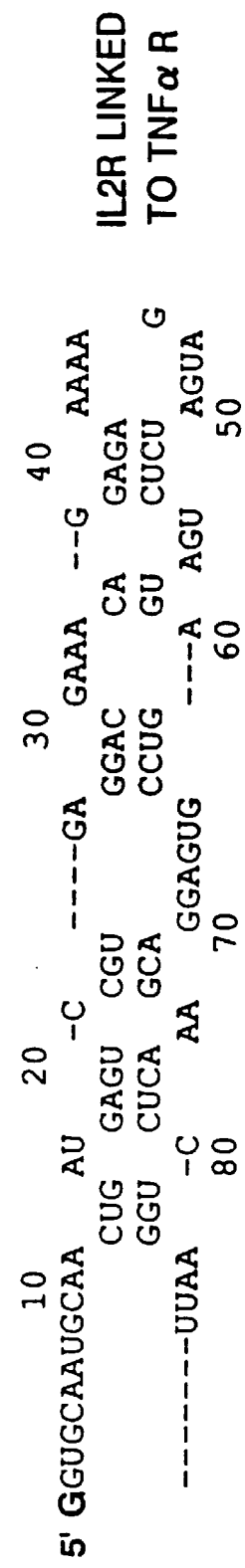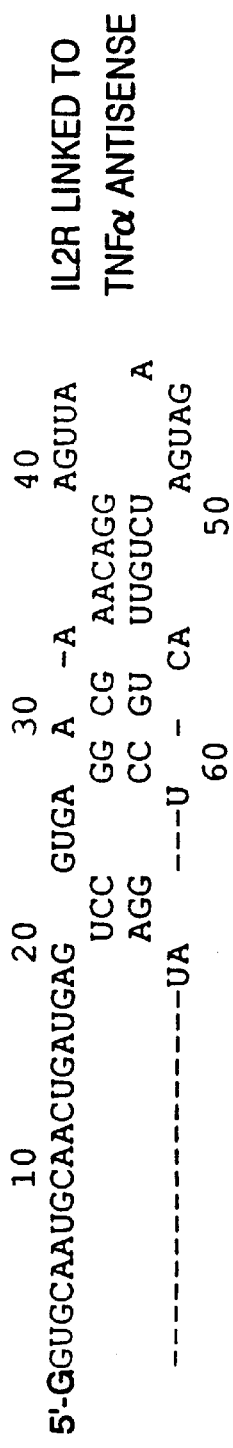

FIGURE 13A

```
         10              20
GUAAGAUGAUCUCUGAUGA     G
                   GUCC  U
                   CAGG  G
- - - - - - - - - UUAAGUUUU    A
         90              30
                             40           50            60
                   GAAACUGCCUGGUACU                       CU
                                   AACCCCUUGGGGCCU   A
                                   UUGGGGAGUUCUGG   A
                   - - - - - - - - - - - - - - - -      CA
                                         80          70
```

FIGURE 13B

```
         10         20            30
GUAAGAUGAUCUCUGAUG   C         ACGA
                  AGU CGUG   AGG
                  UUA GUAC   UCC      A
- - - - - - - - - - - - -  A        GUCA
         90              40
                                   50         60
                                        * CAGC    ACG
                            GGUACUGAAGGC    UCC
                            UCGUGACUUUCG    AGG   U
                                         UACU   CCC
                                             80   70
```

FIGURE 14A
FIGURE 14B
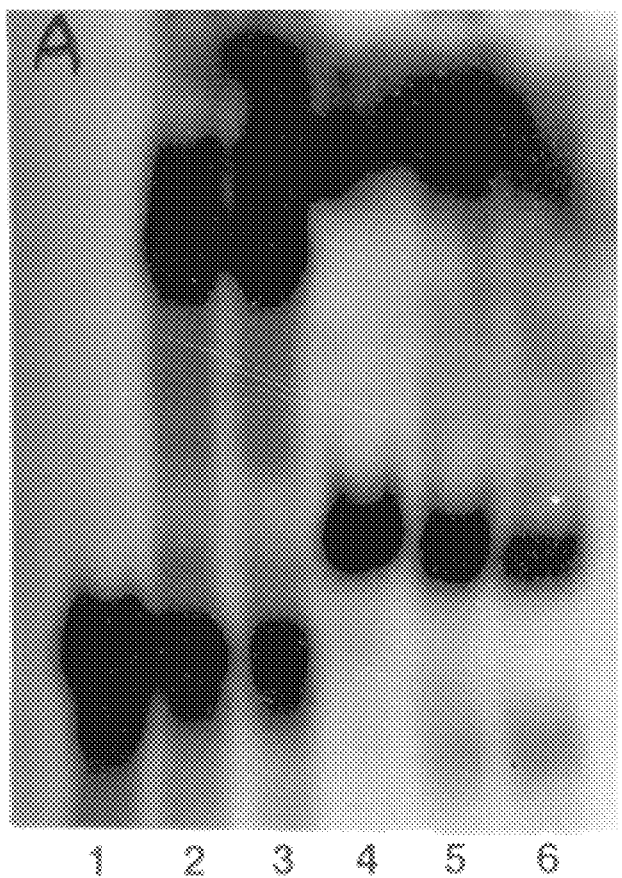
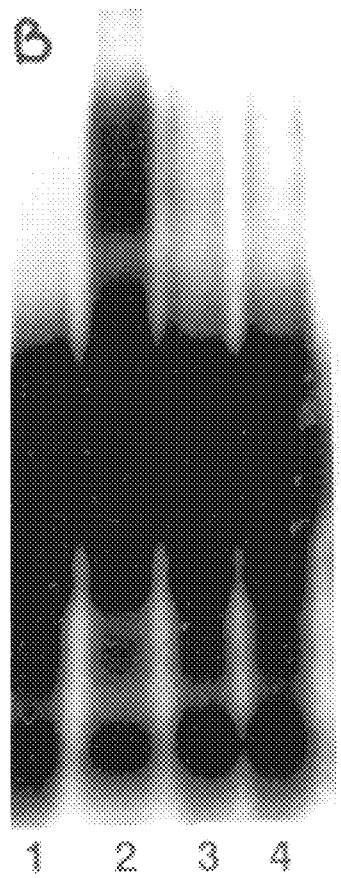

FIGURE 15A

```
           10          20             30
GACUUAGUGCAA       GA   ---A       G
            UGCAACU  UG      GUCC  U
            GCGUUGA  AC      CAGG  G
--------UUAA       GG   AAAG       A
           50          40
```

FIGURE 15B

```
         10
GUAAGA      A    -   AUG
         UG UCUC UG
         GC GGAG GC    A
--UUAA   : A    U  CUG
         :30       20
         :
         :       40
         AAAC   -   -   AUGA
              UGC CUG GU     A
              ACG GAU CA     A
              ----   U  U  GAAA
                    60      50

70            80
              `A        GA   ---A       G
               UGCAACU  UG      GUCC  U
               GCGUUGA  AC      CAGG  G
              -------   GG   AAAG       A
                       100          90
```

FIGURE 17A

```
            10                  20
   GCU   -G     -   -UG   GAC
      GAU   AGU CCG   AG
      UUA   UCA GGU   UC    G
   ---    AA    U   CCG  AAA
       40            30
```

FIGURE 17B

```
           10         20
   GUAAGAUGAUC   GAUGA     G
              UCU     GUCC  U
              AGA     CAGG  G
   --------UUA   ---AG    A
                        30
```

----- THE POTENTIAL BINDING SITE FOR THE PROTEIN(S)

IL2: IL2 RIBOZYME

IL2-TNFα : IL2 RIBOZYME LINKED TO
3' END OF TNFα RIBOZYME

R2 = TNFα RIBOZYME
RA = ANTISENSE LINKED TO TNFα RIBOZYME

C= CONTROL
R2= TNFα RIBOZYME
RA= ANTISENSE LINKED TO TNFα RIBOZYME

TNF-α RIBOZYMES

This application is a continuation-in-part of U.S. Ser. No. 07/971,058, filed Nov. 3, 1992, and now abandoned, and a 371 of PCT/AU93/00567, filed Nov. 3, 1993.

BACKGROUND OF THE INVENTION

Throughout this application, various publications are referred by arabic numerals to within brackets. The disclosures for these publications in their entireties are hereby incorporated by reference into this application to more fully describe the state of the art to which this invention pertains.

The discovery of RNA molecules that possess enzymatic, self-cleaving activity (ribozymes) has provided a new way to artificially control gene expression (Foster & Symons, (1987) Cell, 49:585–591). Ribozymes have been designed that contain nearly all of the sequences required for cleavage. For the hammerhead type, the target RNA needs to contain only the sequence XUX with cleavage occurring 3' from XUX (Haseloff & Gerlach, (1988) Nature, (London) 334:585–591; Perriman et al., Gene (1992) 113: 157–163). The high specificity and limited target requirement give these catalytic RNA molecules the potential for inhibiting viral pathogens and for regulating specific gene expression by interfering with transcription in a highly specific manner (Uhlenbeck, (1987) Nature (London) 328:596–600; Haseloff & Gerlach, (1988) Nature, (London) 334:585–591).

Several reports indicate that the hammerhead type of ribozyme functions in living cells. Cotten & Birnstiel (1989, EMBO J., 8:3861–3866) and Cameron & Jennings (1989, Proc. Natl. Acad. Sci., USA 86:9139–9143) reported ribozyme-mediated destruction and lowering of specific gene expression in Xenopus laevis oocytes and monkey (COS1) cells, respectively. Sarver et al. (1990, Science, 247:1222–1225) showed that a ribozyme directed against HIV-1 gag RNA reduced p24 antigen expression in CD4$^+$ HeLa cells. Recently, this line of study was extended to bacterial cells by showing that a ribozyme designed to cleave the integrase gene of HIV-1 is effective when transcribed from a plasmid in *Escherichia coli*. Integrase RNA was eliminated and integrase protein synthesis was blocked (Sioud & Drlica, (1991) Proc. Natl. Acad. Sci., USA 88:7303–7307). Since ribozymes are effective in vivo, problems of ribozyme stability and delivery may now be addressed.

To interfere with tumor necrosis factor α (TNF-α) gene expression we have used cationic liposome-mediated transfection (Malone et al., (1989) Proc. Natl. Acad. Sci., USA 86:6077–6081) to deliver a ribozyme directed against TNF-α into human promyelocytic leukaemia cells (HL60) and peripheral blood mononuclear cells (PBMNC). TNF-α plays an important role in many inflammatory rheumatic diseases (Shinmei et al., (1989) Sem. Arth. Rheum. 18 (suppl. 1) 27–32), and it modulates the expression of several proteins, including the class I antigens of the major histocompatibility complex (MHC) and cytokines such as interleukin 1 and interleukin 6 (Beutler & Cerami, (1988) Annu. Rev. Biochem. 57:505–518 and (1989) Annu. Rev. Immunol. 7:625–655). TNF-α also appears to be necessary for normal immune responses, but large quantities of it can produce destructive effects such as those seen in rheumatoid arthritis (Brennan et al., (1989) Lancet ii 244–247). In addition, TNF-α is the cytokine responsible for the induction of HIV-1 expression in ACH-2 cells (Rosenberg & Fauci, (1990) Immunol. Today 11:176–180). TNF-α induces the production of cellular factors that bind to the NF-KB enhancer elements within the viral long terminal repeat sequences and thereby activates HIV-1 expression.

The effectiveness of catalytic RNA molecules is dependent on the stability of the mRNA in vivo. In comparison with the knowledge of DNA structural elements, little is known about mRNA stability elements. m-RNA half-lives range from less than 30 minutes for fibroblast interferon and c-fos to greater than 17 hours for β globin. Most eukaryotic mRNAs are protected in cells from exonuclease attack by the 5' cap structure and the 3'poly(A) tail and poly(A) binding proteins. In addition, eukaryotic mRNAs have both 5' and 3' non-coding regions on either side of the coding region. The 5' non-coding region is involved in the rate of initiation of translation of the mRNA to protein. The 3' non-coding region serves to initiate the formation of the poly(A) and can act to stabilize mRNA. (Baralle, F. E., Int. Rev. of Cytology (1983) 81:71–106.) In particular, 3' non-coding iron-responsive elements have been identified that modulate mRNA stability in the presence of iron. Another characterized motif is the AUUUA element responsible for the rapid degradation of some cellular mRNAs, particularly cytokine mRNAs. (Saini, K. S. et al., Mol. Cel. Biochem. (1990) 96:15–23; Ross, H. J. et al., Blood (1991) 77:1787–1795). Some have postulated that an initial endonuclease attack is required, before rapid degradation can take place (Nielson, D. A. and Shapiro, D. J., Mol. Endocrinology (1990) 4:953–957).

There is a need for methods to extend the half-life of particular mRNAs in vivo for protein production and oligonucleotide methods of gene control (antisense and triple helix) for use in plants and animals. Further, stabilizing mRNA elements can be applied to ribozymes in addition to antisense oligonucleotides.

SUMMARY OF THE INVENTION

This invention describes compounds active against TNF-α mRNA. It further describes RNA molecules capable of conferring stability to RNA in vivo through an endogenous protein(s). Possible RNA molecules to be stabilized include ribozymes, antisense molecules, mRNA encoding polypeptides useful for protein production and other cellular RNA. The ribozymes and antisense molecules described herein are useful in mammals and plants, particularly suited for viral diseases. Methods of production and methods of use are also described.

BRIEF DESCRIPTION OF THE FIGURES

FIG. 1A) Ribozyme A is composed of the conserved ribozyme sequence as described by Haseloff & Gerlach (1988), the 5' and 3' flanking sequences complementary to the TNF-α RNA nucleotides 374 and 393: see Pennica et al., (Nature (1984) 312:724–729) for numbering and bacteriophage T7 transcription terminator with CU mispair (C) (Rosenberg et al., Gene (1987) 56:125–135). FIG. 1B) Ribozyme B is identical to A except that it lacks the T7 transcription terminator. FIG. 1C) Ribozyme II is a shortened version of ribozyme B with 9 and 11 base pair hybridizing arms. Antisense RNA is identical to ribozyme A except that it has a single guanosine nucleotide in place of the catalytic domain. The anti-TNF-α hammerhead catalytic gene and antisense RNA control were made as described by Sioud & Drlica ((1991) Proc. Natl. Acad. Sci., USA 88:7303–7307). Briefly, 2 overlapping half oligonucleotides containing the sequences of a bacteriophage T7 RNA polymerase promoter, the 5' and 3' recognition sequences of the ribozyme, the catalytic domain and the T7 transcription terminator were synthesized (an XbaI restriction site was introduced between the T7 terminator and the 3' end of the ribozyme, and PvuII and XhoI sites at the 5' and 3' ends of the ribozyme sequences, respectively), hybridized and then extended with the Klenow fragment of DNA polymerase. Following the extension, DNA was extracted with phenol, precipitated with ethanol, gel purified and then cloned into a SmaI cleaved pUC 18 vector. The sequences of the overlapping primers (Public Health Research Institute, New York 10016, N.Y.) used as follows:

(1) Ribozyme primers (SEQ ID NO:19-22):
5'AACAGCTGTAATACGACTCACTATAGAGTACTAAGATGATCTCTGATGAGTCCGTGAGGACGAAACTGC3' and

5'TTCTCGAGAAAAAACCCTCAAGACCCGTTTAGAGGCCCCAAGGGGTTATGTCTAGACCAGGCAGTTTCGTCC3'

(2) Antisense primers:
5'AACAGCTGTAATACGACTCACTATAGAGTACTAAGATGATCTGACTGCCTGGTCTAG3' and

5'TTCTCGAGAAAAAACCCTCAAGACCCGTTTAGAGGCCCCAAGGGGTTATGTCTAGACCAGCA3'.

The underlined sequences in the figure resulted from the presence of restriction sites in the DNA template. Ribozyme II, unlike ribozyme A and B, lacks these sequences. Therefore, the restriction sequences are not required for stability. Yet, all three of these ribozymes are stable in vivo and bind protein.

Figure 2A:
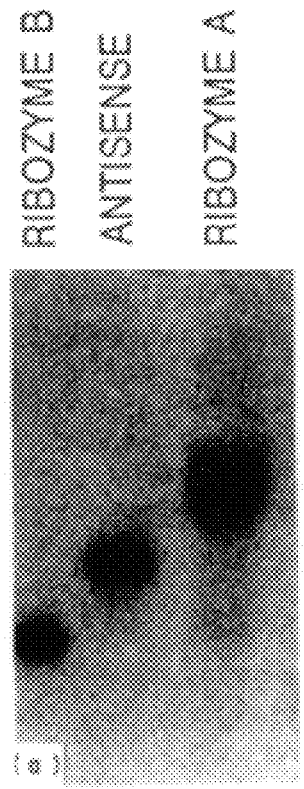
Figure 2B:

FIGS. 2A–2B: A) In vitro RNA transcripts and B) in vitro activity

FIG. 2A) In vitro transcription of ribozymes A, B and TNF-α antisense. Ribozymes and antisense RNA were transcribed with T7 RNA polymerase from PAGE-purified template DNA fragments cleaved from recombinant plasmids as described by (Uhlenbeck, O., Nature (1987) 328:596–600). RNA was labelled internally with [α$^{32}$P]CTP during transcription. Transcription was primed with 7-methyl guanosine (5') triphospho (5') guanosine in all cases. Transcripts were treated with DNAse (RNAse-free), extracted with phenol, precipitated with ethanol and then analyzed by electrophoresis in a 15% polyacrylamide gel containing 7M-urea. The lengths of ribozymes A, B and antisense are 97, 49 and 76 nucleotides, respectively. FIG. 2B) Cleavage of TNF-α RNA in vitro. PBMNC cells are stimulated with PMA and ConA to express TNF-α protein. Whole cell RNA was extracted and the RNA (20 μg) was incubated with 1 μg of either ribozyme or antisense RNA for 60 min. at 50° C. RNA species were then separated by gel electrophoresis and TNF-α RNA was identified by Northern blotting (kb=10$^3$ bases).

Figure 3C:
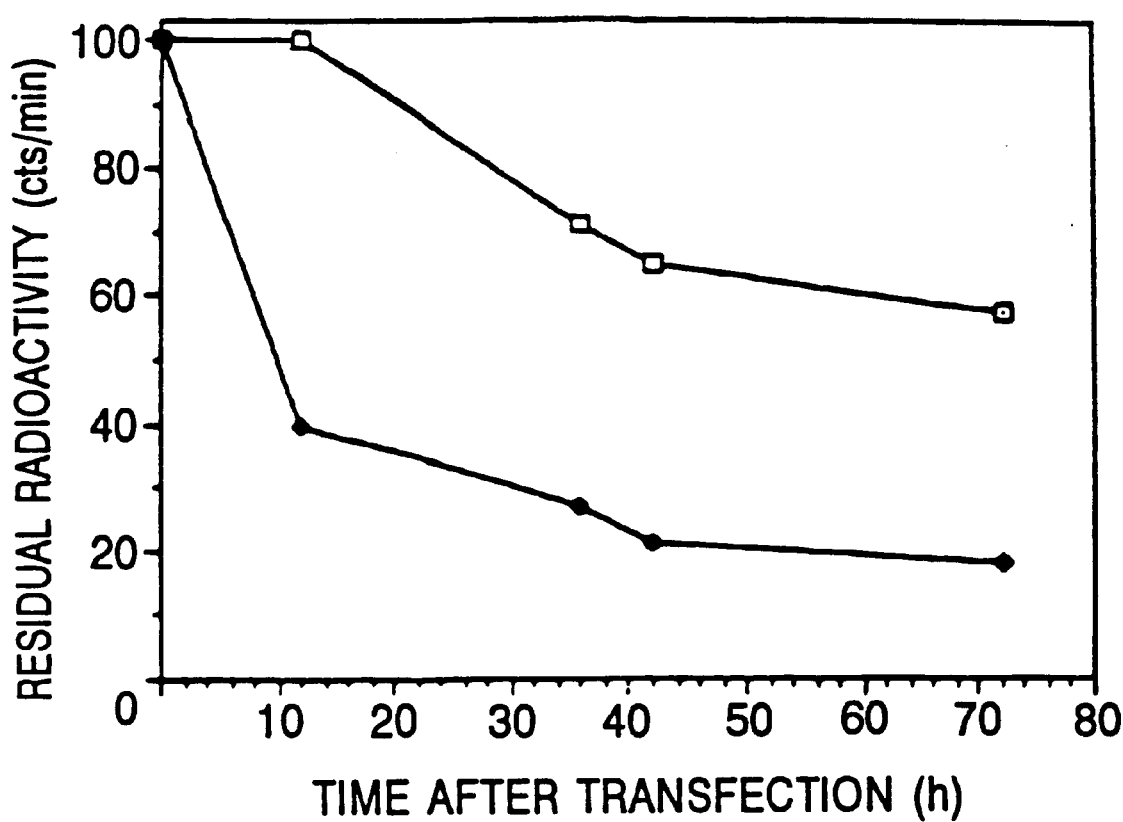

FIGS. 3A–3C: Ribozyme stability following transfection

FIG. 3A) The effect of bacteriophage T7 transcription terminator on RNA stability was compared by cotransfecting HL60 cells with ribozymes A and B. Total RNA was extracted and analyzed by electrophoresis in 15% (w/v) polyacrylamide gels containing 7M-urea. While ribozyme A could be detected more than 72 hours post transfection, the amount of ribozyme B progressively declined (FIG. 3A). The radioactivity contained in each band was then determined, and the results were expressed as the percentage of the radioactivity at zero time. FIG. 3C) shows that ribozyme B decays more rapidly than ribozyme A. The residual radioactivity for ribozyme A and B 72 hours post transfection was 57% and 18% respectively. The stability of the antisense RNA control (ribozyme A lacking the catalytic domain) is similar to ribozyme A (data not shown). Thus, the addition of a bacteriophage T7 terminator to the 3' end of a ribozyme increases it stability.

FIG. 3B) The compartmentalisation of ribozyme A in HL60 cells was also studied by analysis of cytoplasmic and nuclear RNAs. As shown in FIG. 3B) (lanes N and C), ribozyme A is preferentially located in the nucleus.

Ten million human HL60 cells (ATCC CCL 240), growing in log phase in RPMI 1640 supplemented with 20% (v/v) fetal calf serum (FCS), were used for RNA transfection. Cells were washed twice with serum-free medium. A drop (5 ml) of serum free medium was added to polystyrene tubes followed by 35 μg of lipofectin (Bethesda Research Laboratories). 10 μg of carrier RNA (E. coli. tRNA). 3×10$^6$ disints min of $^{32}$P-labelled capped ribozyme A, B or antisense RNA (5 μg). The mixture was immediately mixed. The cells were resuspended in a mixture of serum-free medium lipofectin/RNA/carrier RNA and returned to the incubator for 20 h. Following transfection cells were washed 3 times with Hank's buffered saline solution and then returned to the incubator with RPMI supplemented with 20% FCS. Cells (10$^6$) were harvested at the times indicated above each lane, and total RNA was prepared and analyzed by 15% polyacrylamide gel with 7M-urea. The RNA samples used for transfection are indicated at the top of FIG. 3. Ribozyme B alone serves as a marker to indicate its position in co-transfection experiments. 3B) Analysis of nuclear (N) and cytoplasmic (C) RNA. A sample (50 μM) of labelled, capped ribozyme A was used to transfect HL60 cells for 20 h. Cells were washed 3 times, and the nuclear and cytoplasmic RNAs were prepared and analyzed by gel electrophoresis. For preparation of cytoplasmic and nuclear fractions, the cells were homogenized in 10 mM-Tris·HCl (pH 7·5). 5 mM-KCl, 140 mM-NaCl, 5 mM-dithiothreitol and 0.49% (w/v) Nonidet P40 for 10 min at 4° C. and the nuclei were collected by centrifugation at 800 g for 5 min. RNA in the supernatant fluid was precipitated and saved as the cytoplasmic fraction. The nuclei were processed as described by Chomezynski & Sacchi (1987, Anal. Biochem. 162:156–160) for total RNA preparation. The arrow indicated the position of ribozyme A monomer. 3C) one experiment showing RNA quantification. The run amount of radioactivity in the ribozyme bands shown in 3A) was determined and expressed as a percentage of the radioactivity present immediately after 20 h transfection time. □ Ribozyme A: ♦ ribozyme B.

Figure 4:
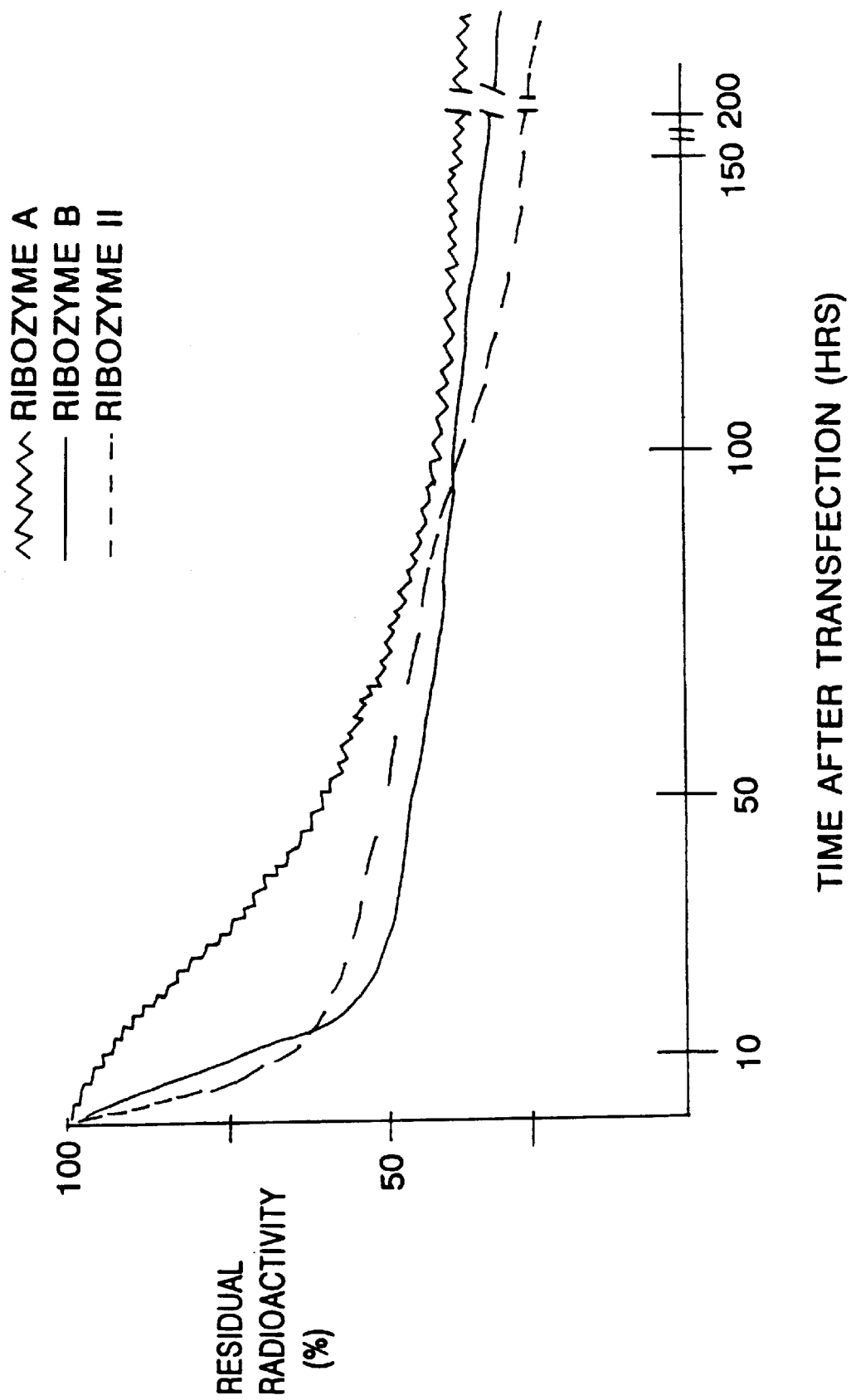

FIG. 4: Stability of ribozyme A, B and II in HL60 cells.

Mean of more 50 experiments, ribozymes were introduces to the cells using the DOTMA cationic liposome-mediated transfection. Following transfection cells were washed and resuspended in complete media. Cells contained in 1 ml culture were harvested at various times. Total RNA was prepared and then analyzed by 15% polyacrylamide gel containing 7M urea. The amount of ribozyme radioactivity was normalized to actin mRNA or ribosomal RNA and then expressed as a percentage of the radioactivity present after 16 hours post-transfection time. These experiments were repeated 50 times for some time points as opposed to FIG. 3C) which was just a single experiment. Further, reexamination of FIG. 3C) showed parallel curves for ribozyme A and B indicating similar stability for ribozyme B.

Figure 5B:
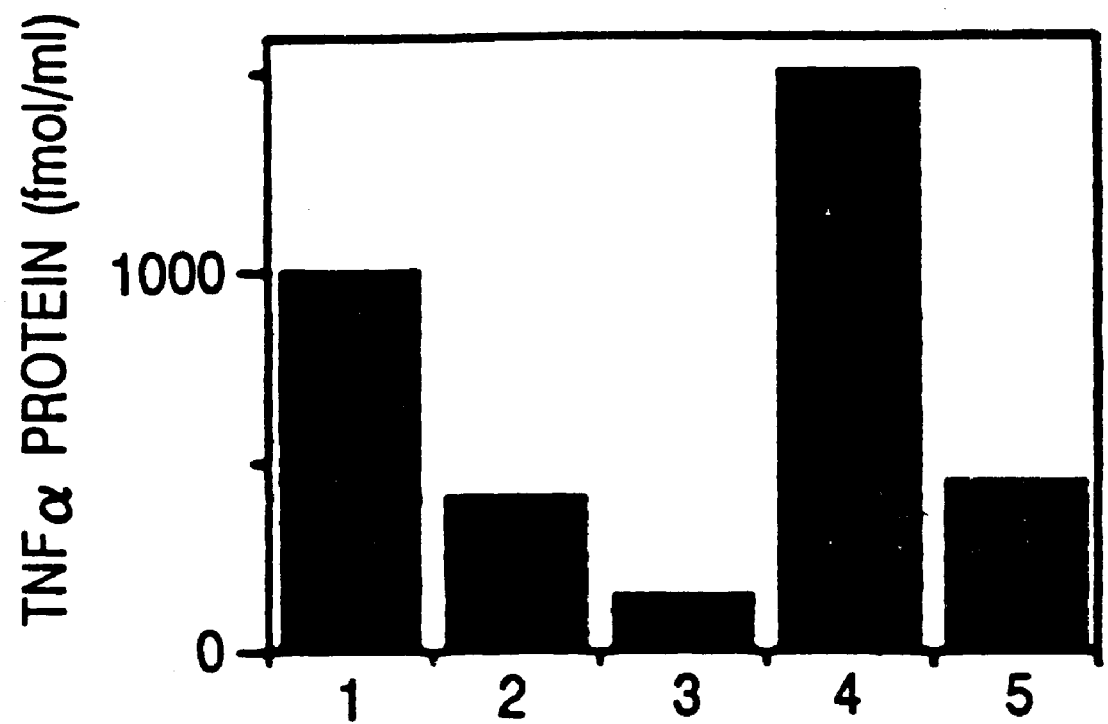

FIGS. 5A–5B. Ribozyme activity in vivo.

FIG. 5A) Ribozymes and antisense RNA activities in HL60 cells 5A) were analyzed after a transfection period (20 h). Following transfection with ribozyme A or antisense RNA, cells were stimulated for 6 h to express TNF-α. RNA was extracted, separated by gel electrophoresis through a 1–2% (w/v) agarose form-aldehyde gel, and detected by Northern blotting with radioactive probe for the TNF-α gene. After hybridization with TNF-α probe, the filter was stripped and then hybridized with an actin probe (British Biotechnology Limited), in the case of peripheral blood mononuclear cells PBMNC. Cells were separated (Sioud et al., 1990) and washed 4 times with Hank's buffered saline solution and 3 times with serum-free medium. Cells ($10^6$) were transfected and processed as HL60 cells. Lanes 1 and 4, controls (transfected only with carrier RNA 1 μg E. Coli tRNA); lane 2, antisense RNA; lanes 3 and 5, ribozyme A. This auto-radiogram was overexposed to display the TNF-α signal in ribozyme A lanes. FIG. 5B) Radioimminoassay to TNF-α protein. Ionomycin was used during stimulation step to release the TNF-α protein into the medium. The amount of TNF-α protein present in the media was determined using the TNF-α [$^{125}$I] assay system (Amersham). Lanes 1 to 5 correspond to lanes 1 to 5 in FIG. 5A) and 5B), respectively.

Figure 6A:
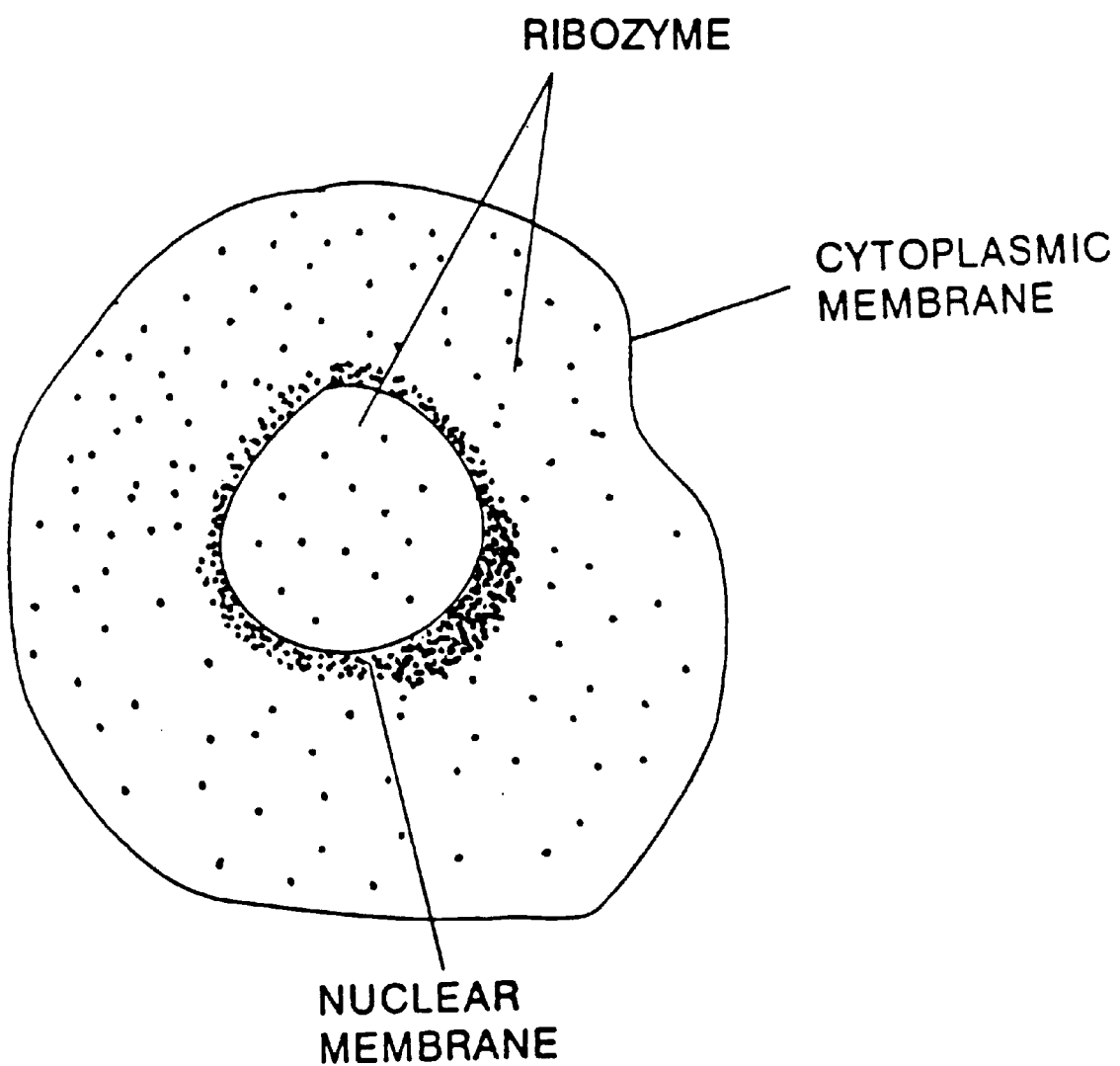
Figure 6B:
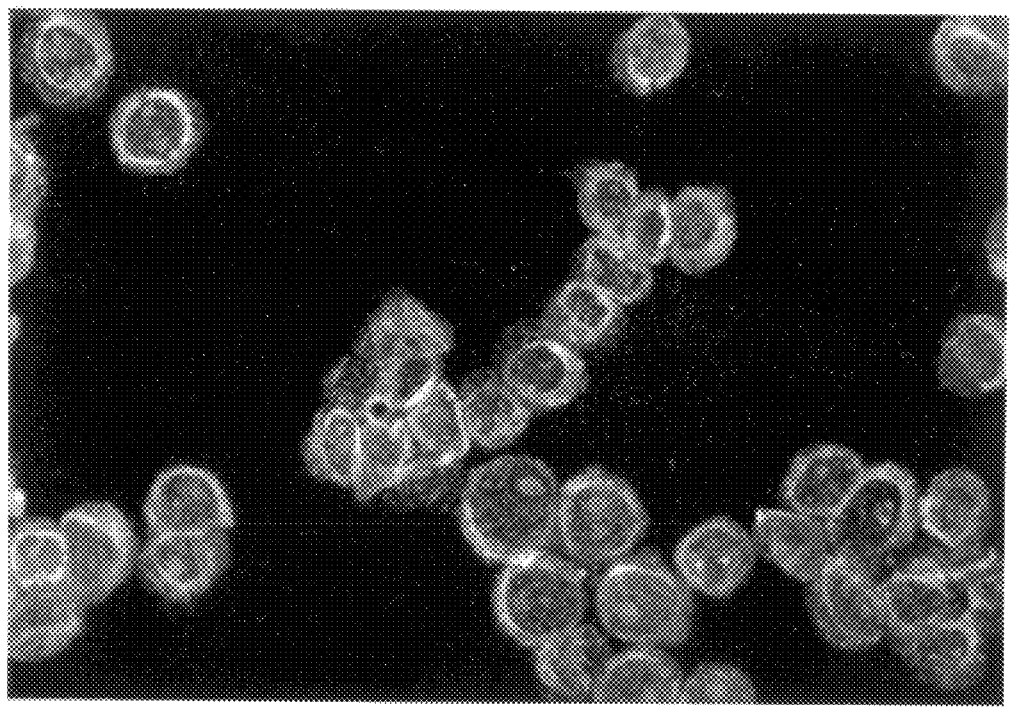

FIGS. 6A–6B: Tmmunostaining of the ribozyme B and II in HL60 cells.

FIG. 6A shows digoxigenin conjugated uridine was incorporated into the ribozymes during transcription. Cells were transfected with Digoxigenin-conjugated ribozymes. Following transfection microscope slides were prepared and then the ribozyme inside the cells were detected with anti-Digoxigen-fluorescein Fab conjugate. FIG. 6B shows a photo of the fluorescent cells.

Figure 7A:
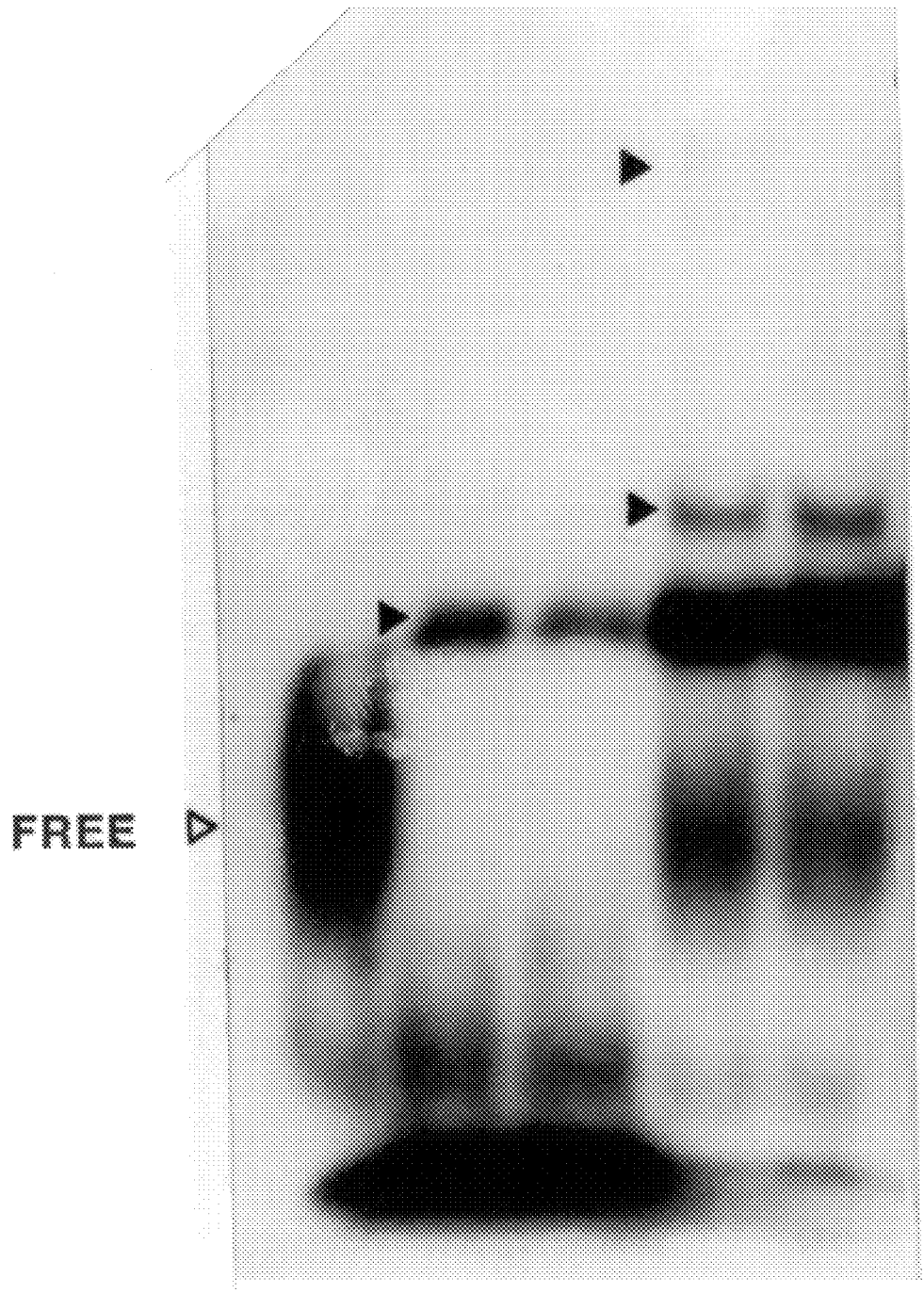

FIGS. 7A–7C: Gel retardation assay of cytoplasmic extracts from HL60 cells and PBMNC with TNF-α ribozymes II and B.

FIG. 7A) Ribozyme II was incubated at RT for 25–30 minutes (lanes 2,3,4 and 5) (see below) or not (lane 1) with extract proteins an then analyzed by electrophoresis (25 μg oligo+5 μg cytoplasmic extract (CE)). Lanes 4 and 5 are as lanes 2 and 3 respectively, but 20 units of RNAsin was added. All complexes seen in lanes 4 and 5 could be seen in lanes 2 and 3 (original film).

FIG. 7B) 25 ng of TNF-α ribozyme II was generated by in vitro transcription as.described previously (Sioud, et al., 1992) and incubated at room temperature for 25 minutes with cytoplasmic extracts (CE) prepared from HL60 or PBMN cells as described in materials and methods. Following incubation, the protein ribozyme complexes were separated by 4% polyacrylamide native gel. lane 1: control without CE; lane 2: +5 μg CE from HL60 cells; lane 3: as lane 2, but in addition 1 ug of tRNA was added; lane 4 as lane 3, but in addition 10 units of Rnase inhibitor was added; lane 5 as lane 4, but before electrophoresis the sample was treated with proteinase k; lane 6 as lane 1, but 5 ug of the CE from PBMN cells was added; lane 7 as lane 6, but more 1 ug of tRNA was added; lane 8 contains the ribozyme RNA recovered from the high molecular complex (The complex was excised from one preparative gel, the materials were eluted and then phenol extracted.

FIG. 7C) gel retardation with ribozyme B: As panel A ribozyme B and incubated (lane 2) with 5 ug of CE prepared from HL60 cells.

Figure 8:
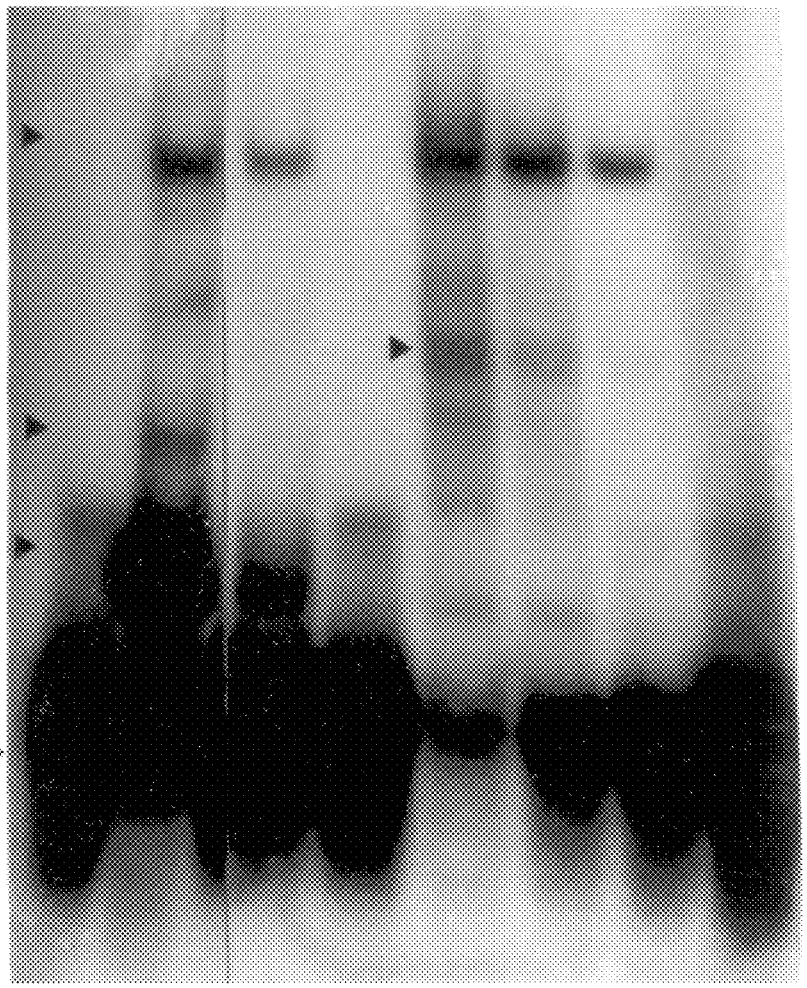

FIG. 8: Competition assays 25 ng of ribozyme II was incubated with 5 ug of cytoplasmic protein from HL60 cells or PBMN as described in FIG. 5. Lane 1 control without CE, lane 2 as lane 1, but both 5 ug of CE from HL60 cells and 2500 ng of polydCdI were added; lane 3 as lane2, but instead of polydC dI 2500 ng of cold ribozyme was added; lane 4 as lane 3, but 500-fold excess of cold ribozyme was added; lane 5 as lane 1, but 5 ug of CE from PBMN cells was added; lanes 6, 7, 8 as lane 5, but 300, 400 or 500 of cold ribozyme was added, respectively.

FIGS. 9A–9C: Predicted secondary structures (9A) Interleukin 2 (IL-2) ribozyme, and IL-2 ribozyme linked to the 5' end of TNF-ribozyme (9B) or antisense (9C) (SEQ ID NO:23–25).

Figure 10A:
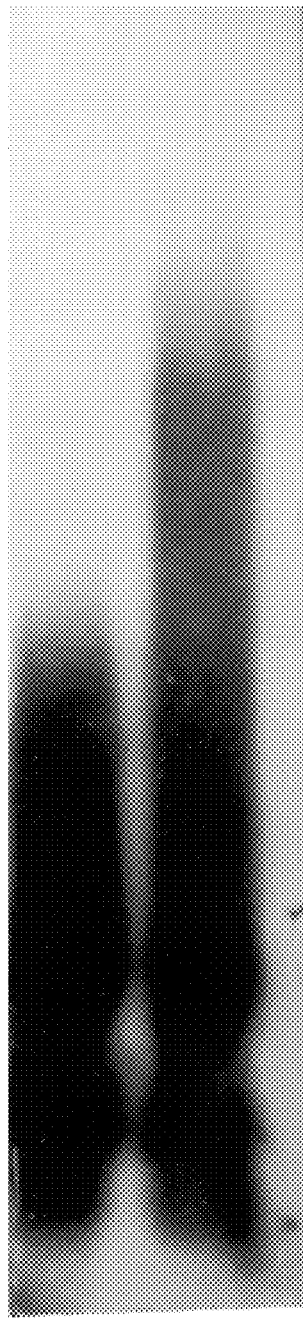
Figure 10B:
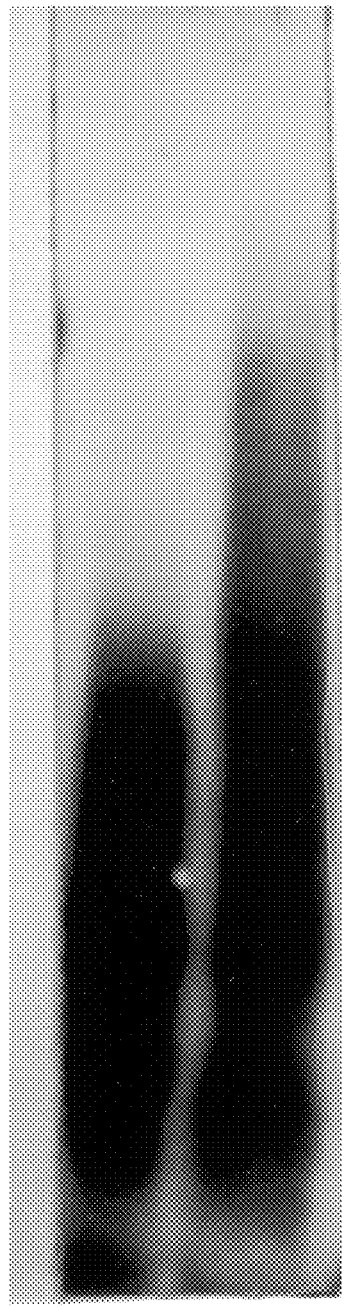

FIGS. 10A–10B: Gel retardation assay of cytoplasmic extract with IL-2 ribozymes.

FIG. 10A) 25 ng of IL-2 ribozyme generated by in vitro transcription was incubated with CE from HL60 cells; lane 1 control without CE; lane 2 with CE from HL60 cells.

FIG. 10B) Instead of CE with HL60 cells, IL-2 ribozyme was incubated with CE from PBNM cells (lane2).

Figure 11A:
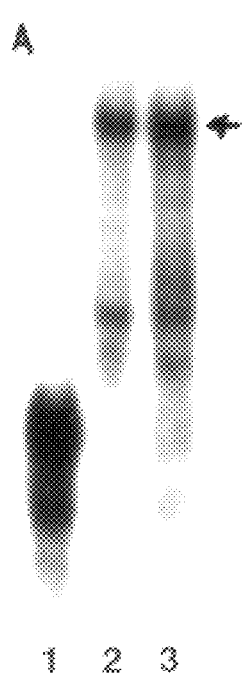
Figure 11B:
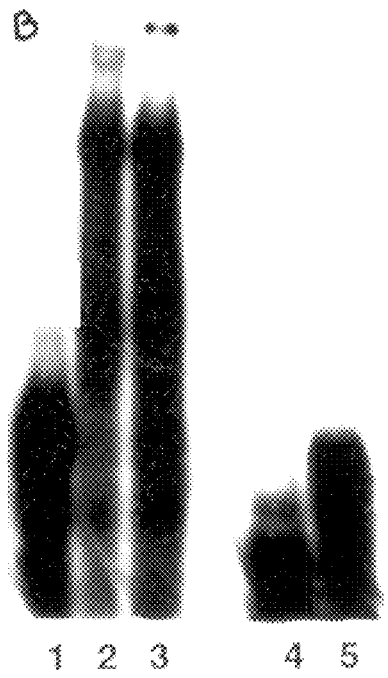
Figure 11C:
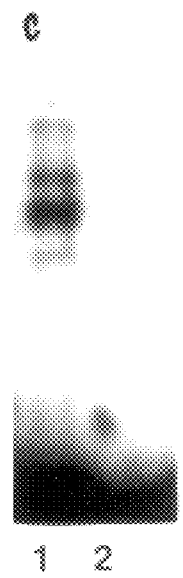

FIGS. 11A–11C: Gel retardation and UV crosslinking experiments.

FIG. 11A) 50 ng of TNF-α ribozyme II generated by in vitro transcription was incubated at room temperature for 25 minutes with cytoplasmic extracts (CE) prepared from PBMN cells. Following incubation the protein ribozyme complexes were separated by 6% polyacrylamide native gel. Lane 1 control without CE; lane 2: +5 μg CE1 from PBMN cells; lane 3: +5 μg CE2 from PBMN cells. Lanes 4 and 5 as lanes 2 and 3 respectively, but are treated with proteinase K for 15 minutes prior electrophoresis. CE1 and CE2 correspond to two different cytoplasmic protein preparations.

FIG. 11B) The same panel as A, but overexposed.

FIG. 11C) The region of the gel containing the complex as indicated by arrow was cut from the native gel, exposed to UV for 30 min, soaked in tris buffer, treated with ribonuclease Ti and analyzed on 10% SDS polyacrylamide gel.

Figure 12A:
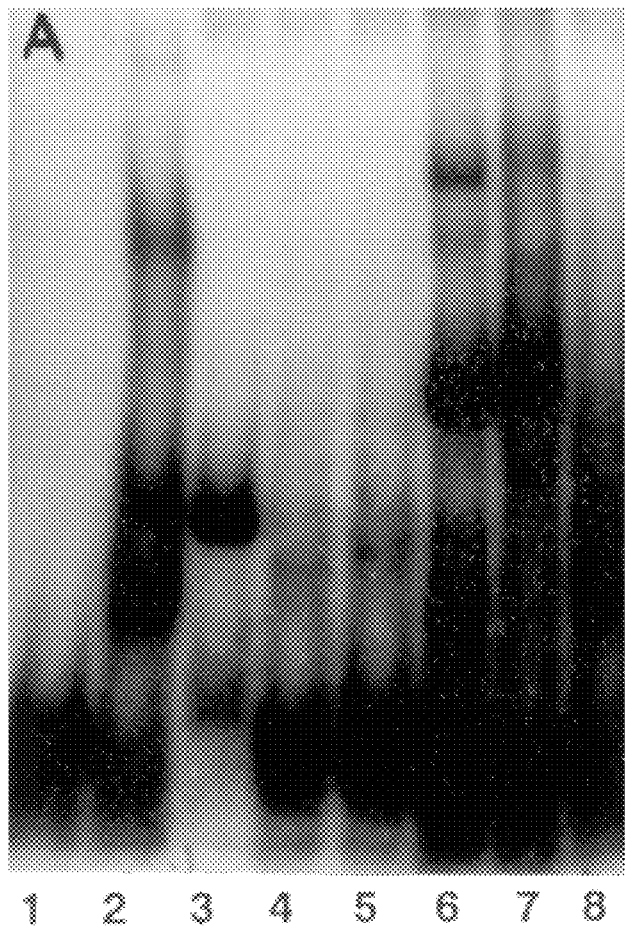

FIG. 12A: Gel retardation with IL-2 ribozyme, IL-2 linked ribozyme linked to the 5' of TNF-α ribozyme.

Figure 12B:
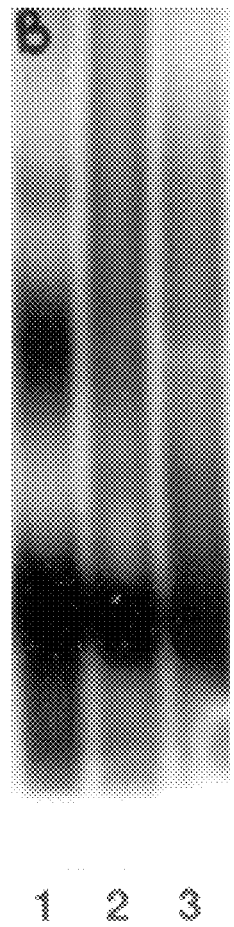

50 ng of TNF-α ribozyme, IL-2 ribozyme, IL-2 linked ribozyme to the 5' of TNF-α ribozyme or IL-2 linked to the 5' TNF-α antisense were incubated at room temperature with two different cytoplasmic extracts (CE1 and CE2) prepared from PBMN cells:

Lane 1: TNF-α ribozyme–CE as control; lane 2 TNF-α ribozyme+CE; lane 3 IL-2 ribozyme–CE as control; lane 4: IL-2 ribozyme+CE; lane 5: IL-2 ribozyme+CE2; lane 6: IL-2 ribozyme linked to the 5' end of the TNF-α ribozyme–CE; lane 7: IL-2 ribozyme linked to the 5' end of the TNF-α ribozyme+CE1; lane 8: IL-2 ribozyme linked to the 5' end of the TNF-α ribozyme+CE2;

FIG. 12B: Gel retardation with IL-2 linked to the 5' TNF-α antisense.

Lane 1:IL-2 ribozyme linked to the TNF-α antisense–CE; lanes 2 and 3 IL-2 ribozyme linked to the TNF antisense+2 μg CE1 or 5 μg CE respectively.

FIGS. 13A–13B: Predicted secondary structures FIG. 13A) T7 terminator linked to TNF-α ribozyme. FIG. 13B) TNFα antisense linked to the 3' end of the TNF-α ribozyme (SEQ ID NO 26–27). ★ In order to obtain the folding for the antisense molecule two As were added at the junction.

FIG. 14A: Gel retardation using TNF-α ribozyme or TNF antisense linked to TNF-α ribozyme.

50 ng of TNF-α ribozyme II or TNF antisense linked to TNF ribozyme generated by in vitro transcription were incubated at room temperature for 25 minutes with cytoplasmic extracts (CE) prepared from PBMN cells.

Lane 1: TNF-α −CE as control; lane 2: TNF-α+CE; lane 4: TNF antisense linked to TNF-α ribozyme−CE as control; lane 5 and 6 as lane 4, but incubated with CE1 and CE2 respectively.

FIG. 14B: Competition experiments.

Lane 1: control−CE; lane 2+CE; lane 3 as lane 2, but 300 excess of cold TNF-α ribozyme was added to the reaction, lane 4 as lane w, but 500 of cold TNF-α ribozyme was added to the reaction.

FIGS. 15A–15B: Predicted secondary structures 15A) IL-2 ribozyme and 15B) IL-2 ribozyme linked to the 3' end of the TNF-α ribozyme (SEQ ID NO 28–29).

Figure 16:
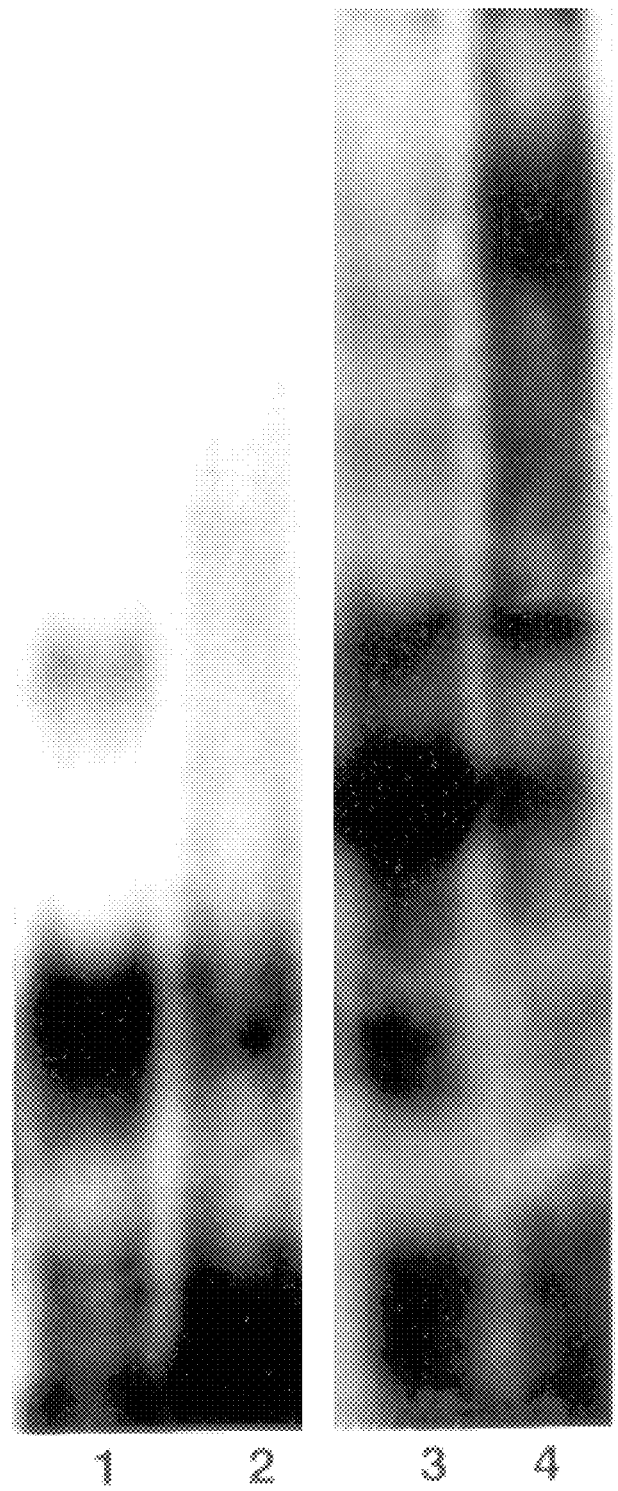

FIG. 16: Gel retardation using IL-2 ribozyme or IL-2 ribozyme linked to the 3' of TNF-α ribozyme.

50 ng of IL-2 ribozyme and IL-2 ribozyme linked to the 3' of TNF-α ribozyme generated by in vitro transcription were incubated with or without cytoplasmic extract for 25 minutes at room temperature.

Lane 1: IL-2 ribozyme−CE as control; lane 2 as lane 1, but +CE; lane 3: IL-2 Ribozyme linked to the 3' end of TNF-α ribozyme−CE as control; lane 4 as lane 3 but +CE. The electrophoresis mobility of the IL-2 ribozyme and IL-2 linked to TNF-α was not reproducible, presumably due to intramolecular interactions.

FIGS. 17A–17B: Predicted secondary structures 17A) TNF-α ribozyme truncated at the 5' end and 17B) the TNF-α ribozyme truncated at the 3' end (SEQ ID NO 30–31).

FIGS. 18A–18D: Gel retardation using TNF-α ribozyme, the 3' or 5' truncated TNF-α ribozyme and the integrase ribozyme.

Figure 18A:
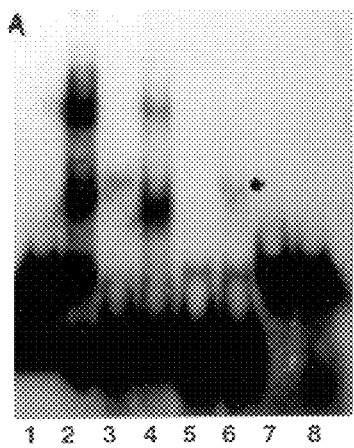

FIG. 18A) 50 ng of TNF-α ribozyme, the 3' or 5' truncated TNF-α ribozyme and the integrase ribozyme generated by in vitro transcription were incubated at room temperature for 25 minutes with cytoplasmic extracts (CE) prepared from PBMN cells.

Lane 1: TNF-α ribozyme−CE; lane 2; TNF-α ribozyme+ CE; lane 3; a 3' truncated TNF-α ribozyme−CE as control; lane 4: as lane 3 but+CE; lane 5: a 5' truncated TNF-α ribozyme−CE as control; lane 6: as lane 5, but+CE; lane 7: integrase ribozyme−CE as control; lane 8: as lane 7, but+CE.

Figure 18B:
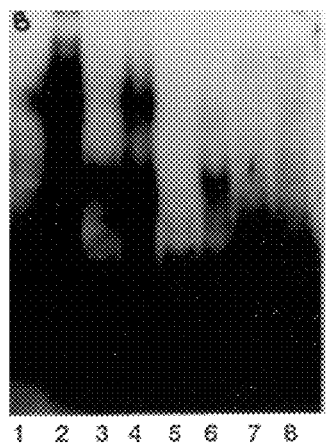
Figure 18C:
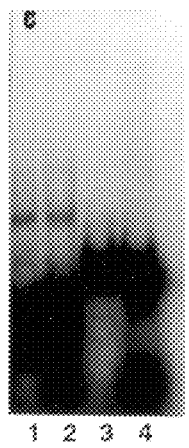

FIG. 18B) As panel A, but overexposed.

C) Lane 1: the 5' truncated TNF-α ribozyme−CE as control; lane 2 as lane 1, but+CE; lane 3: integrase ribozyme−CE as control; lane 4 as lane 3, but+CE.

Figure 18D:
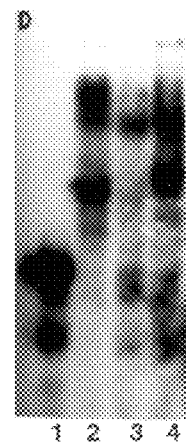

FIG. 18D) 25 ng of the 3' truncated TNF-α ribozyme generated by in vitro transcription were incubated at room temperature for 25 minutes with cytoplasmic extracts prepared from different cell types.

Lane 1:−CE as control; lane 2: as lane 1, but incubated with CE prepared from PBMN cells; lane 3: as lane 1, but incubated with CE prepared from HL60 cells; lane 4: as lane 1 but+CE prepared from WH164 cells.

Figure 19A:
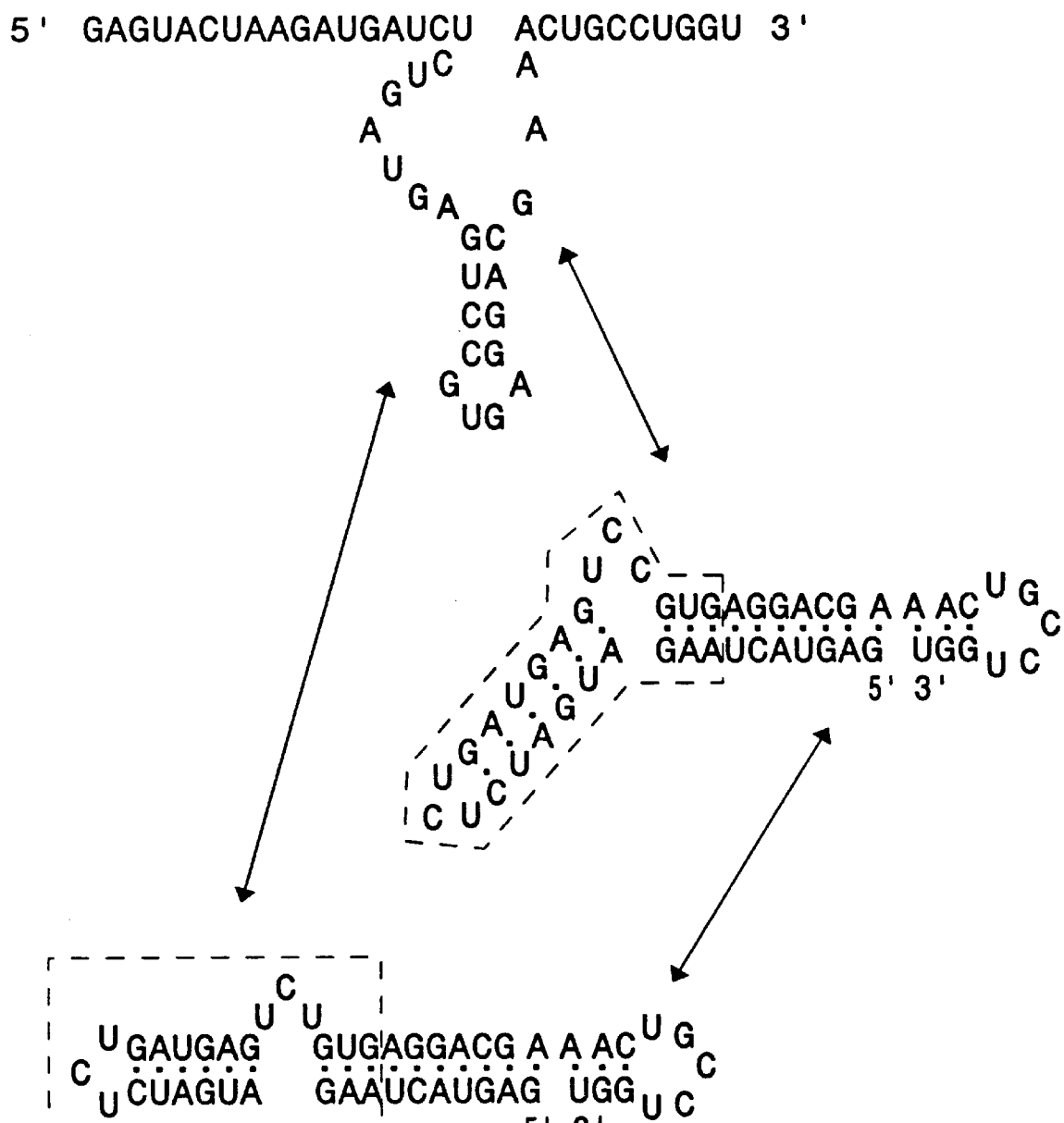
Figure 19B:
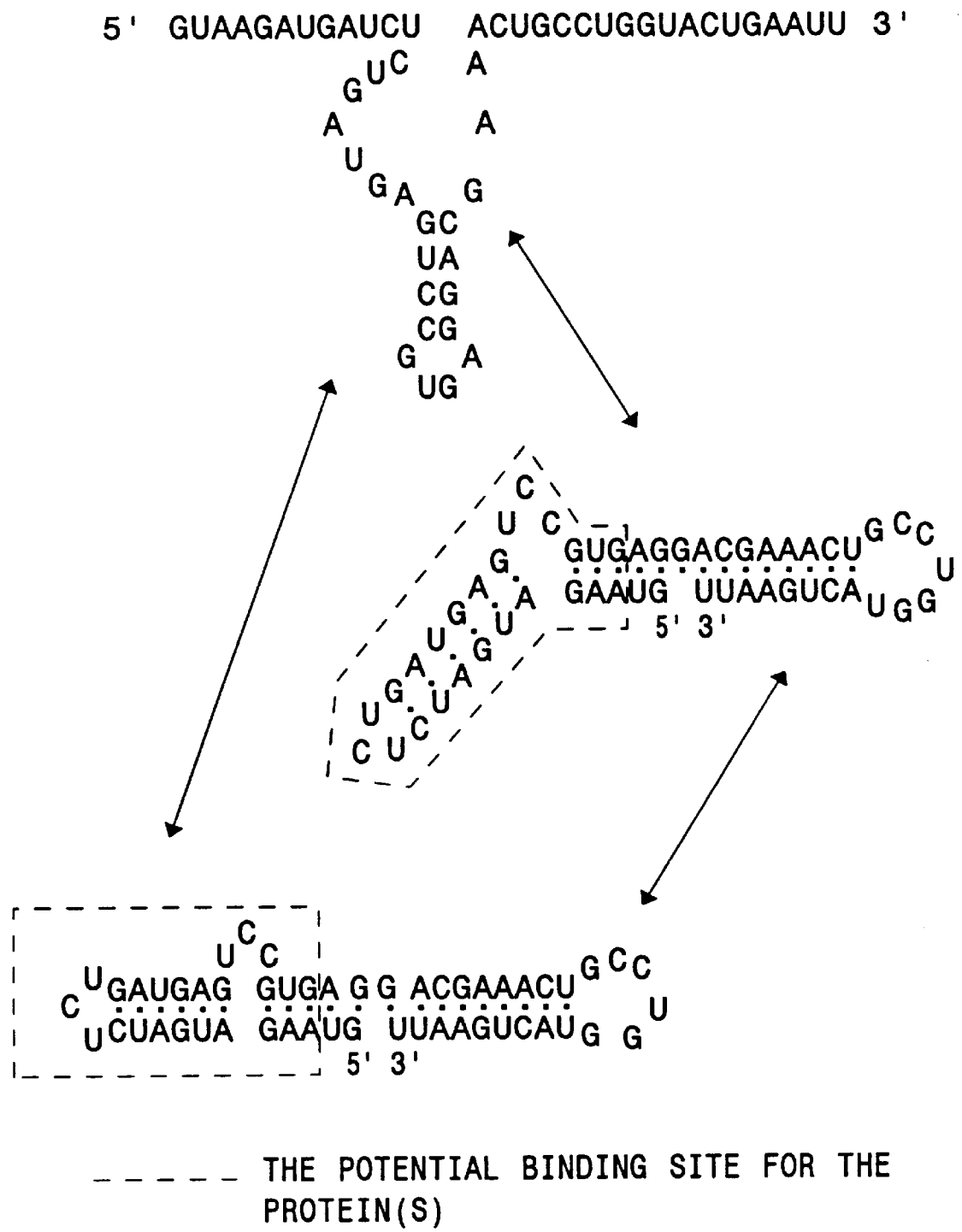

FIG. 19: Potential binding sites for protein on TNF-α ribozyme B (SEQ ID NO 32) and TNF-α ribozyme II.

Figure 20:
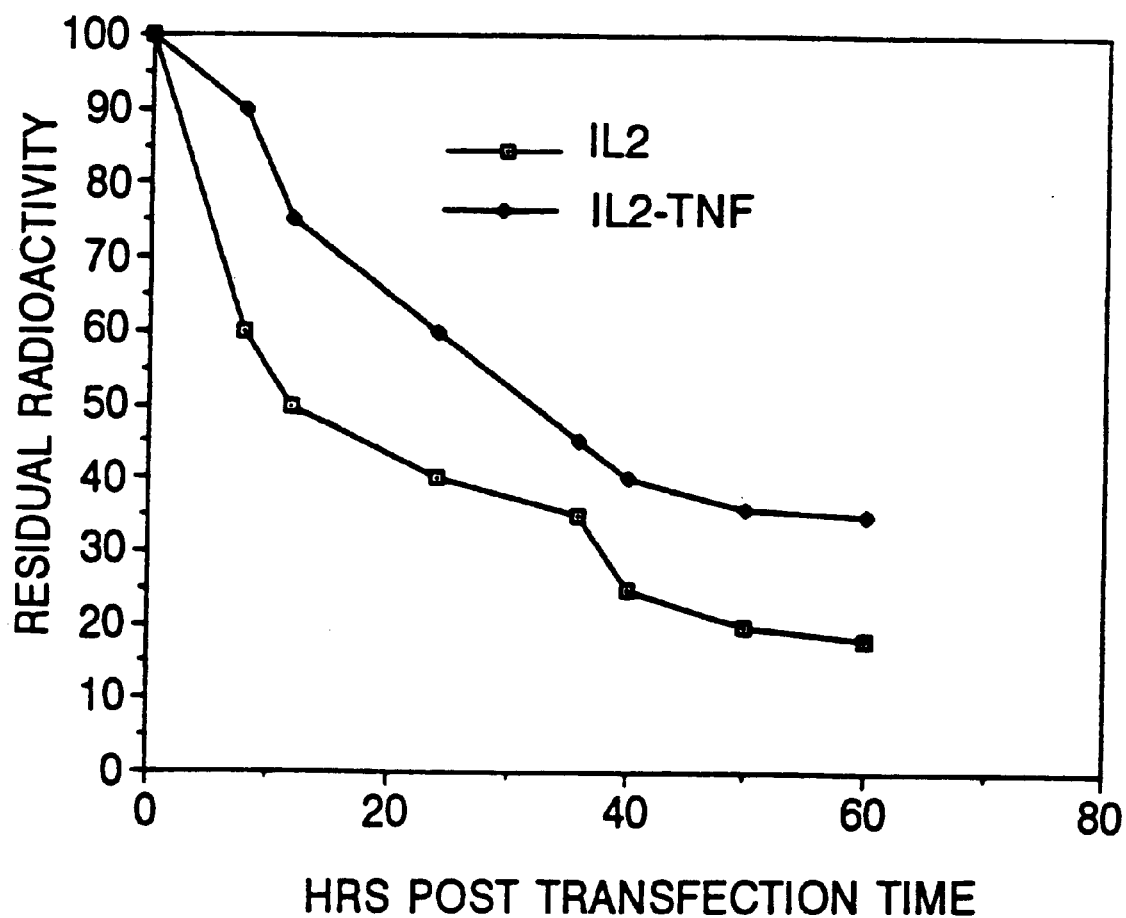

FIG. 20: In vivo activity of IL-2 ribozyme and IL-2 ribozyme linked to the 3' end of the TNF-α ribozyme.

Figure 21A:
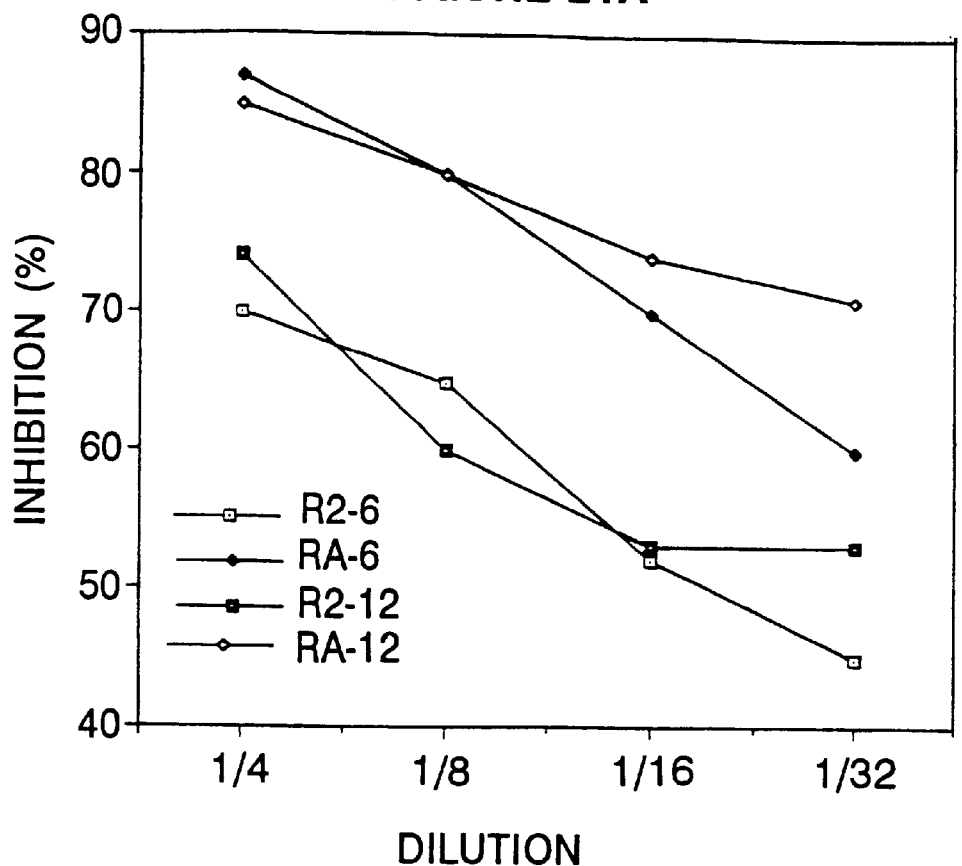
Figure 21B:
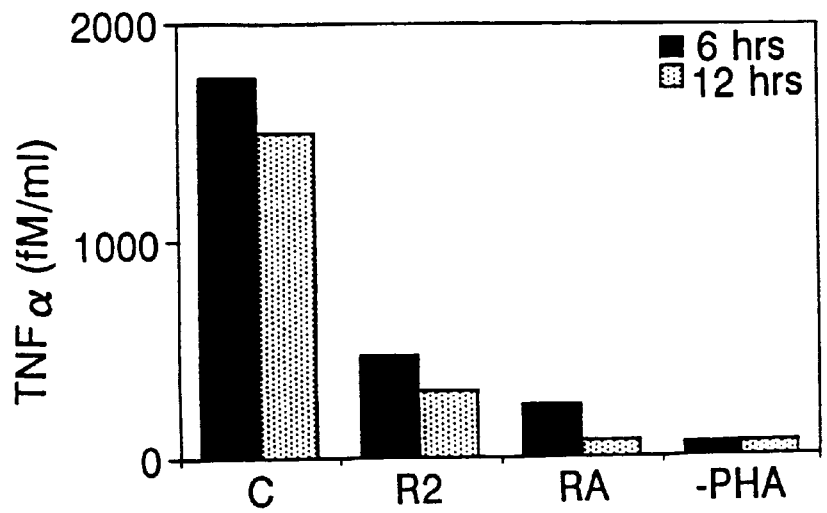

FIGS. 21A–21B: In vivo activity of the TNF-α ribozyme and the TNF-α antisense linked to the 3' end of the TNF-α ribozyme.

FIG. 21A) Cytotoxicity assay at 6 and 12 hours transfection time.

FIG. 21B) Quantification of the TNF-α levels by radioimmunoassay.

Figure 22:
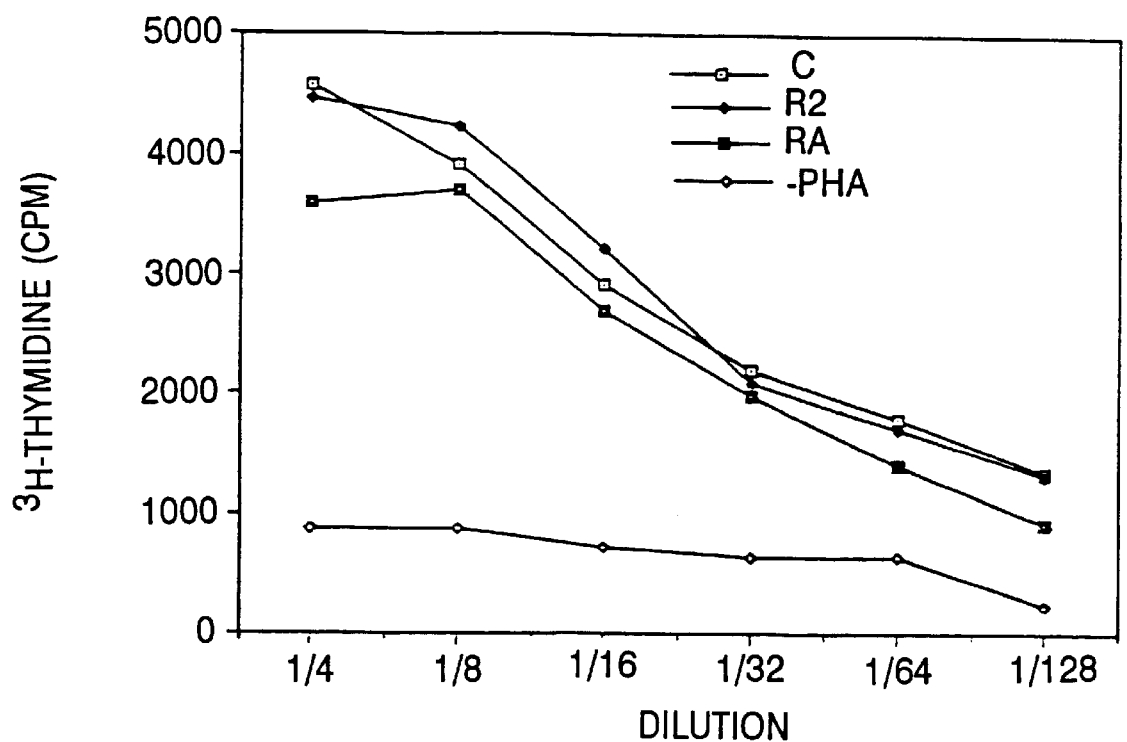

FIG. 22: Qaantification of in vivo levels of IL-2 by CTLL2 assay (see text).

Figure 23:
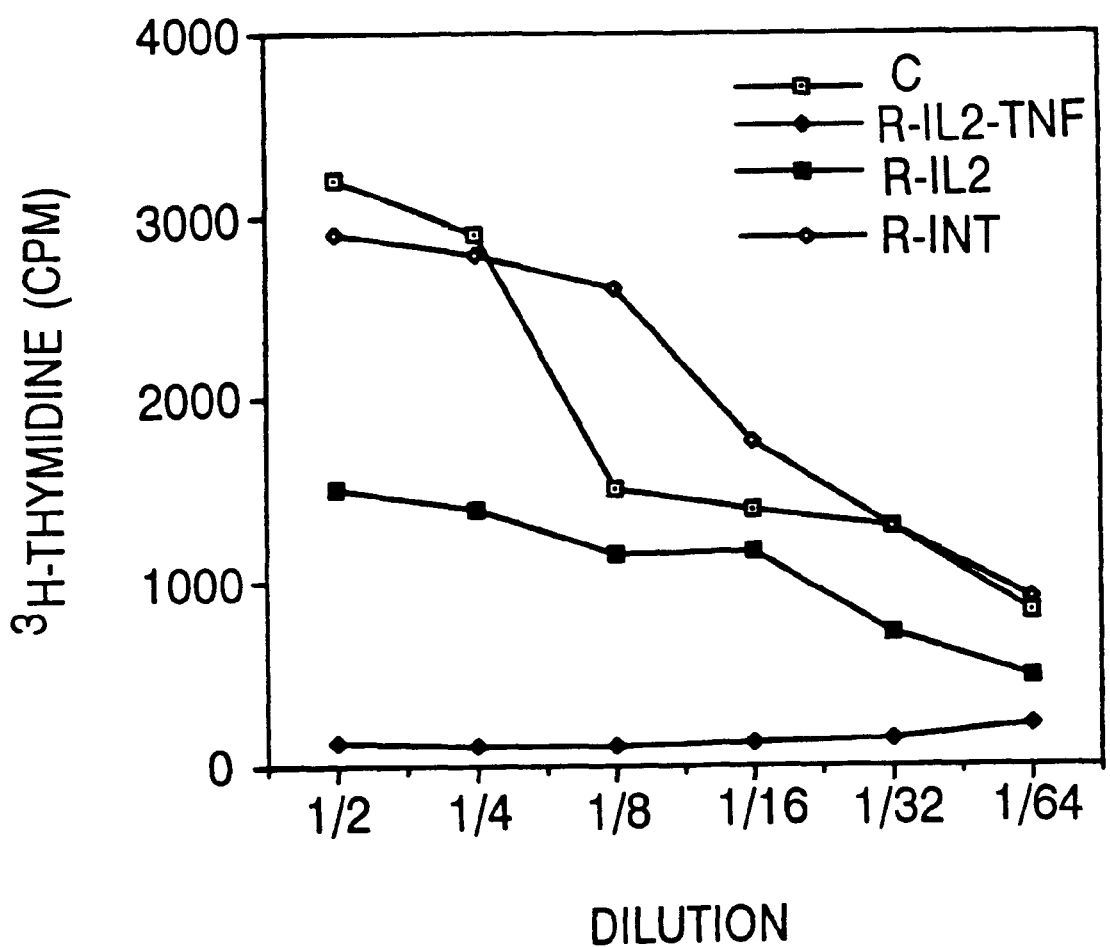

FIG. 23: Effect of TNF-α ribozyme and antisense on IL2 gene expression.

DETAILED DESCRIPTION OF THE INVENTION

The invention described herein relates to TNF-α ribozymes or compounds having the structure (SEQ ID NO:1):

$$3'—(X)_n \text{ ggu(t)ccgu(t)cA} \qquad \text{u(t)cu(t)agu(t)agaa}(X)_{n'}—5'$$

wherein each X represents a ribonucleotide or a deoxyribonucleotide which is the same or different and may be modified or substituted in its sugar, phosphate or base; wherein each of A, C, U, and G represents a ribonucleotide and a, c, u(t), and g represents a ribonucleotide or deoxyribonucleotide which may be unmodified or modified or substituted in its sugar, phosphate or base; wherein each of $(X)_n$ and $(X)_{n'}$ represents an oligonucleotide having a predetermined sequence; wherein each of n and n' represents an integer from 0 to 100; wherein each 0 represents base pairing between the nucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1 and typically less than 100; wherein each of the dashed lines independently represents either a chemical linkage providing covalent bonds between the nucleotides located on either side thereof or the absence of any such chemical linkage; and wherein $(X)_b$ represents an oligonucleotide which may be present or absent with the proviso that b represents an integer which is greater than or equal to 2 if $(X)_b$ is present.

Such compounds are targeted for cleaving the TNF-α mRNA in vivo. Site directed mutagenesis in the hybridizing arms ggu(t)ccgu(t)cA and u(t)cu(t)agu(t)agaa (SEQ ID NO:2) is possible provided that sufficient complementarity is maintained so that the compound hybridizes to the TNF-α mRNA in vivo. All RNA compounds are also part of the invention as are compounds with DNA arms and an RNA catalytic region.

Also part of the invention are compounds in which $(X)_n$ or $(X)_{n'}$ is absent. One form of the compound described above has the structure below (SEQ ID NO:3):

$$3'-(X)_n \text{ ggu(t)ccgu(t)cA} \qquad \text{u(t)cu(t)agu(t)agaa-5'}$$

where the nucleotides are defined as above. An all RNA version of the compound is also described. Further the compound may have the structure (SEQ ID NO:4):

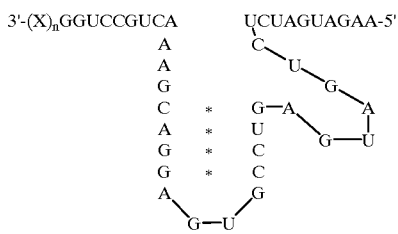

wherein (X)n represents an oligoribonucleotide.

Further the compound may have the structure (SEQ ID NO:27) where the 3' end is a TNF-α antisense molecule targetted for a different target on the TNF-α gene.

3'-UUAAGUACUCGUGACUUUCGUAC-

-UAGGCCCUGCACCUCGACCGGAA-

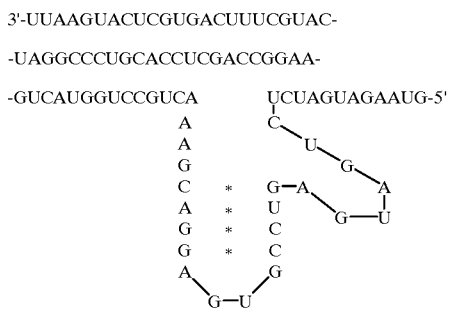

The invention further includes a compound which is a multiple ribozyme having the structure:

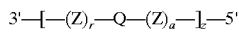

wherein each Q represents the compounds above which may be the same or different; wherein each Z represents a ribonucleotide or a deoxyribonucleotide which is the same or different and may be modified or substituted in its sugar, phosphate or base; wherein each of r and s represents an integer which may be greater than or equal to 0; and wherein z represents an integer greater than or equal to 1.

Further, this invention relates to compounds and methods for increasing protein production by increasing the steady state level of mRNA by decreasing the rate of intracellular degradation of an mRNA of interest. Such compounds and methods are useful for increasing the stability, and therefore effectiveness, of ribozymes and antisense RNA. The compounds and methods of this invention also can be utilized to increase the production of proteins by increasing the quantity of mRNA available to be transcribed.

Ribozymes are RNAs capable of catalyzing RNA cleavage reactions. One of the simplest and most commonly used are the hammerhead type ribozymes which contain a conserved catalytic domain and flanking sequences that hybridize with the substrate RNA (Haseloff et al. PCT International Publication No WO 89/05852). Hammerhead ribozymes can be targeted against any RNA sequence that contains an XUX triplet amenable for cleavage. Several studies have demonstrated the ability of these ribozymes to cleave a target RNA in vivo and suppress protein expression. Other classes of ribozymes are tetrahymena IVS (Group I Intron) (Cech et al. U.S. Pat. No. 4,740,463, issued Apr. 26, 1988), RNAse P (Altman et al. PCT International Publication No WO 92/03566), hepatitis delta ribozymes (e.g. Blumenfeld et al. PCT International Application No. WO/90/05157) and hairpin ribozymes (European Patent Application No. EP 360, 257, Hampel et al. Nuc. Acids Res. (1990) 18:299–304).

The stabilized mRNAs of the claimed invention may be further stabilized using methods in the literature for example the use of transcription terminators on the 3' end such as the T7 terminator, ρ-independent terminator, cry element (Gelfand et al. U.S. Pat. No. 4,666,848, issued May 19, 1987) or the TrpE terminator. Furthermore, sequences such as the poly(A) addition signal AATAAA may be added and strategies involving changing the length of the 3' non-coding region (see Gillies, U.S. Pat. No. 5,149,635, issued Sep. 22, 1992). These techniques can be used to stabilize mRNA for ribozyme, antisense, or protein production purposes.

Specifically, this invention encompasses RNA molecules capable of conferring stability on single stranded RNA represented by the $(X)_n$ and $(X)_{n'}$ of interest which have the structure (SEQ ID NO:5):

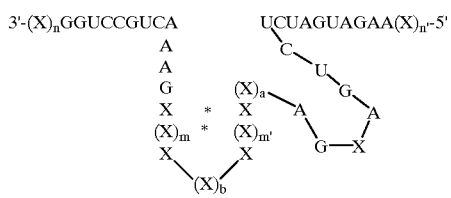

wherein each X represents a ribonucleotide which may be the same or different; wherein each of $(X)_n$ and $(X)_{n'}$ represents an oligonucleotide having a predetermined sequence; wherein each of n and n' represents an integer from 0 to 1000; wherein each 0 represents base pairing between the ribonucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligoribonucleotide with the proviso that b represents an integer which is greater than or equal to 2.

Another embodiment of the invention is an RNA molecule having the structure (SEQ ID NO:6):

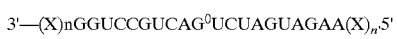

wherein each X represents a ribonucleotide which may be the same or different; wherein $G^0$ may be present or absent; and $(X)_n$ and $(X)_{n'}$ are as defined above.

As described above site directed mutagenesis is possible in the GGUCCGUCA and UCUAGUAGAA (SEQ ID NO:7) respectively in either the TNF-α ribozyme or the TNF-α antisense structure. Because the arms are binding the RNA binding in vivo considerable variations are possible. Compounds missing either the 3' or the 5' arm are also encompassed within the invention describe herein. Preferably, the 5' arm is missing. Also preferably the compounds are linked to the 3' end of the TNF-α ribozyme. In one embodiment multiple versions of the 3' end of the TNF-α ribozyme are used as stabilizing elements.

In one embodiment of the invention (X). or (X).. encodes at least one ribozyme. The ribozyme may be a hairpin ribozyme, RNAase P, or more preferably a hammerhead ribozyme. In the case wherein $(X)_n$ or $(X)_{n'}$ encodes at least one hammerhead ribozyme it may have the structure (SEQ ID NO:8):

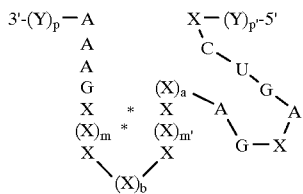

wherein each of X and Y represents a ribonucleotide which may be the same or different; wherein each of $(Y)_p$ and $(Y)_{p'}$ represents an oligonucleotide having a predetermined sequence which is capable of hybridizing with an RNA target sequence to be cleaved; wherein each of p and p' represents an integer which defines the number of ribonucleotides in the oligonucleotide with the proviso that the sum of p+p' is sufficient to allow the ribozyme to hybridize with the RNA target sequence; wherein each 0 represents base pairing between the ribonucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligoribonucleotide with the proviso that b represents an integer which is greater than or equal to 2.

In embodiment of the invention the RNA molecule may have the following structures (SEQ ID NO:9,10):

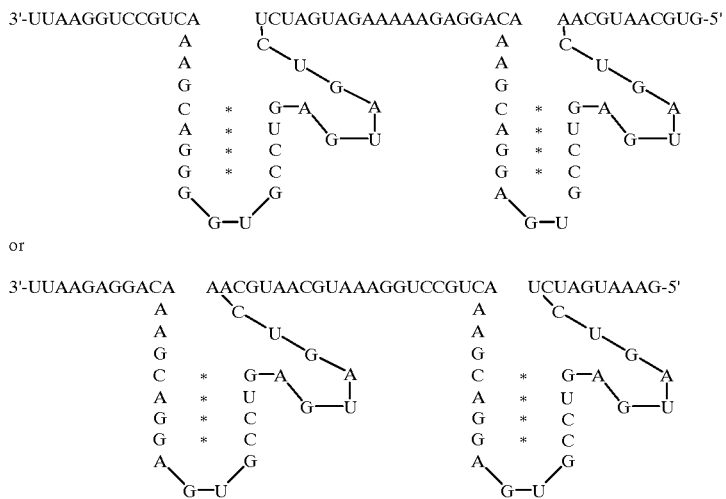

Additional embodiments of the invention may have the following structures (SEQ ID NO:11–13):

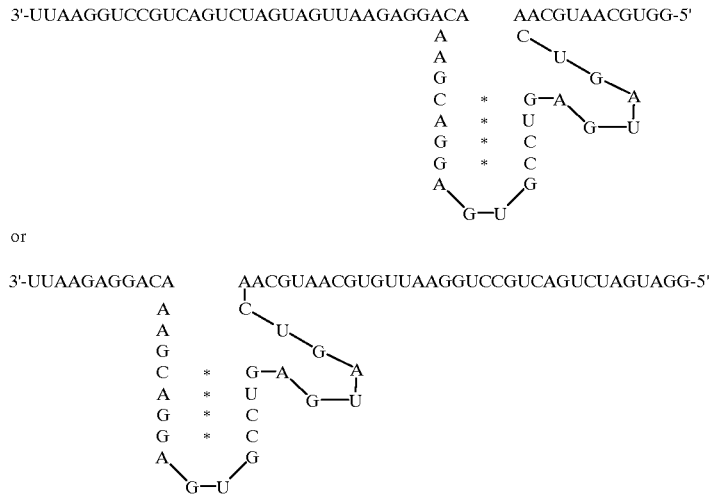

For the specific IL-2 ribozymes above one with skill in the art will recognize that other linkers are possible.

Alternatively, $(X)_n$ or $(X)_{n'}$ may have the structure:

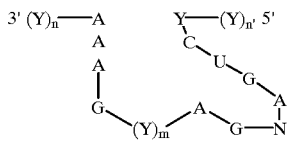

wherein each Y represents a ribonucleotide or a deoxyribonucleotide which is the same or different and may be modified or substituted in its sugar, phosphate or base; wherein $(Y)_n$ and $(Y)_{n'}$ represent oligonucleotides in which n and n' are integers which define the number of nucleotides in the oligonucleotides, such oligonucleotides having predetermined sequences sufficiently complementary to a predefined RNA target sequence to be cleaved to allow hybridization to the RNA target sequence, such predefined RNA target sequence not being present within the compound; wherein N may be adenine, guanine, cytosine or uracil; wherein each solid line represents a chemical linkage providing covalent bonds between the nucleotides located on either side thereof; wherein M represents an integer from 2 to 20; and wherein none of the nucleotides (Y), are Watson-Crick base-paired to any other nucleotide within the compound.

Another embodiment of the invention is the RNA molecule described above may also be used to stabilize an mRNA which encodes a polypeptide. Particularly, the RNA compounds are useful for the production of proteins of industrial or commercial significance. Many such proteins are either already available commercially or are under commercial development. Example such proteins include human and animal growth hormones, tissue plasminogen activators, erythropoietin, and factor VIII.

The invention may be employed to improve the production of such protein in cell culture, particularly in an-animal cell culture such as CHO cells grown in culture. Thereby one could reduce the substantial costs involved in commercial production of such proteins.

Another embodiment of the invention $(X)_n$ or $(X)_{n'}$ a ribozyme capable of cleaving targets. Alternatively, $(X)_n$ or $(X)_{n'}$ is an antisense sequence capable of hybridizing to an RNA indigenous to a mammal or plant and thereby deactivating it (for plants see Shewmaker et al. U.S. Pat. No. 5,107,065, issued Apr. 21, 1992). Further, the targets for the ribozyme or antisense sequence may be a viral gene including viral targets such as cytomegalovirus, hepatitis, herpes, HIV, EBV, papilloma virus, cytomegalovirus, rhinovirus, influenza virus, varicella-zoster virus, parainfluenza virus, mumps virus, respiratory syncytial virus, adenovirus, measles virus, rubella virus, human parvovirus, poliovirus, rotavirus, echovirus, arbovirus, or human T cell leukemia-lymphoma virus.

The invention also embodies methods of production of the compounds and RNA molecules described above comprising the steps of: (a) ligating into a transfer vector comprised of DNA, RNA or a combination thereof, a nucleotide sequence corresponding to said compound; (b) transcribing the nucleotide sequence of step (a) with RNA polymerase; and (c) recoverin g the compound. The invention also includes transfer vectors, bacterial or phage, comprised of RNA or DNA or a combination thereof containing a nucleotide sequence which on transcription gives rise to the compounds or RNA molecules described above.

Further, many methods have been developed for introducing cloned eukaryotic DNAs into cultured oamhmalian cells (Sambrook et al. Molecular Cloning: A Laboratory Manual 2ed. Cold Spring Harbor Laboratory Press 1989): Calcium phosphate- or DEAE-dextran-mediated transfection; Polybrene; Protoplast fusion; Electroporation; and Direct microinjection into nuclei.

The invention provides a method f or treating a disorder associated with over expression of TNF-α which comnprises administering to a subject an effective amount of the TNF-α ribozyme so as to reduce the overexpression of TNF-α and thereby treat the disorder. Such disorders include rheumnatic arthritis, AIDS, septic shock, graft versus host disease, the cachexia associated with cancer and autoimmune diseases.

The invention also provides a method of cleavage or deactivation of a specific RNA target sequence using the RNA molecules described above. Such RNA sequences may be indigenous to a mammal or a plant. It is particularly suited for targetting viral genes such as HIV (see Goodchild et al. U.S. Pat. No. 4,806,463, issued Feb. 21, 1989).

in the compounds and methods described herein the respective 5' and 3' termini of the groups $(X)_n$ and $(X)_{n'}$ imay be modified to stabilize the endonuclease from degradation. For example, blocking groups may be added to prevent terminal nuclease attack, in particular 3'–5' progressive exonuclease activity. By way of example, blocking groups may be selected from optionally sub stituted alkyl, optionally substituted phenyl, optionally substituted alkanoyl. Optional substituents may be selected from C1–C5 alkoxy and the like. Altenatively, nucleotide analogues such as phosphorothioates, methyiphosphonates or phosphoramidates or nucleoside derivatives (such as α-anomers of the ribose moiety) which are resistant to nuclease attack may be employed as terminal blocking groups.

Alternatively, non nucleic acid groups which alter the susceptibility of the endonuclease molecule to other nucleases may be inserted into the 3' and/or 5' end of the endonuclease. For example, 9-amino-acridine attached to the endonuclease may act as a terminal blocking group to generate resistance to nuclease attack on the endonuclease molecules and/or as an intercalating agent to aid endonucleolytic activity. It will be readily appreciated that a variety of other chemical groups, e.g. spermine or spermidine could be used in a related manner.

Endonucleases of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the endonucleases of the present invention may be associated with RNA binding peptides or proteins which may assist in bringing the endonuclease into juxtaposition with a target nucleic acid such that hybridization and cleavage of the target sequence may take place. Nucleotide sequences may be incorporated into the 5' and 3' ends of the groups $(X)_n$ and $(X)_{n'}$ to increase affinity for substrates. Such additional nucleotide sequences may form triple helices with target sequences (Strobel, S. A., et al., (1991) Nature 350:172–174 and references therein which are incorporated by reference) which may enable interaction with intramolecularly folded substrate. Alternatively, modified bases (non-natural or modified as described in Principles of Nucleic Acid Structure, Supra bases within the additional nucleotide sequences may be used that will associate with either single stranded or duplex DNA generating base pair, triplet, or quadruplet, interactions with nucleotides in the substrate. Suitable bases would include inosine, 5'-methylcytosine, 5'-bromouracil and other such bases as are well known in the art, as described, for example, in Principles of Nucleic Acid Structure, Supra.

Synthetic preparations of mRNA are well known (see Sambrook et al. Molecular Cloning: A Laboratory Manual 2ed. Cold Spring Harbor Laboratory Press 1989). Mixed DNA-RNA oligomers with modified base pairs for the TNF-α ribozyme can be prepared by commercially available DNA synthesizers such as those produced by Applied Biosystems, Biosearch, or Milligen(see, e.g., Perrault et al., Nature, 344:565–567 (1990, for derivatives Uhlmann, E. and Peyman, A. Chemical Reviews (1990) 90:543–584, H-phosphonate monomers see Agrawal et al. U.S. Pat. No. 5, 149,798).

The proteins which bind the conserved TNF-α motif may serve to increase the rate and specificity of the ribozyme reaction. Recently, Tsuchihashi et al. reported that the p7 nucleocapsid (NC) protein accelerates the rate of cleavage of a hammerhead ribozyme by 10–20 fold (Science (1993) 262:99–102). Accordingly, the protein which binds the TNF-α motif may have a similar effect.

An "effective amount" as used herein refers to that amount which provides a desired effect in a mammal having a given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the oligonucleotide, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multimellar vesicles, erythrocyte ghosts, or spheroplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamic acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and oligonucleotides coupled to antibodies directed against tissue-specific receptors, ligands or antigens or coupled to ligands of tissue-specific receptors. Further, specific nucleotide sequences may be added to target the oligonucleotides of this invention to the nucleus, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, aerosols, or other inhalants. The oligonucleotides may be encapsulated in a wafer, wax, film or solid carrier, including chewing gums. Permeation enhancers to aid in transport of movement across the epithelial layer are also known in the art and include, but are not limited to, dimethyl sulfoxide and glycols.

This invention is illustrated in the Experimental Detail section which follows. These sections are set forth to aid in an understanding of the invention but are not intended to, and should not be construed to, limit in any way the invention as set forth in the claims which follow thereafter.

EXPERIMENTAL DETAILS

Targeted ribozymes cut TNF-α RNA in vitro

Figure 1A:
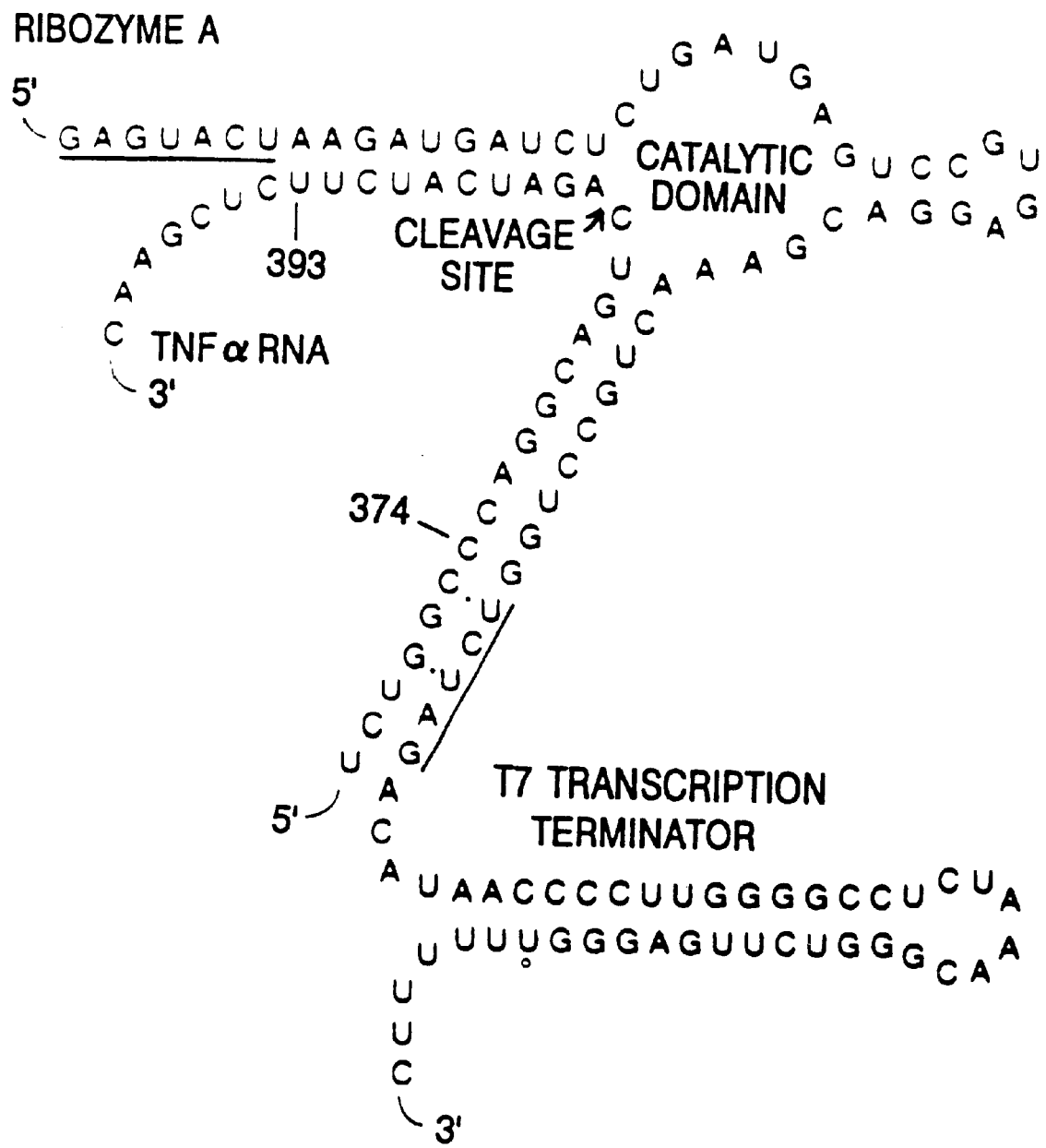
FIGS. 1A–1C: Base-pairing of ribozyme A, B and II with TNF-α RNA template (SEQ ID NO:15–18)
Figure 1B:
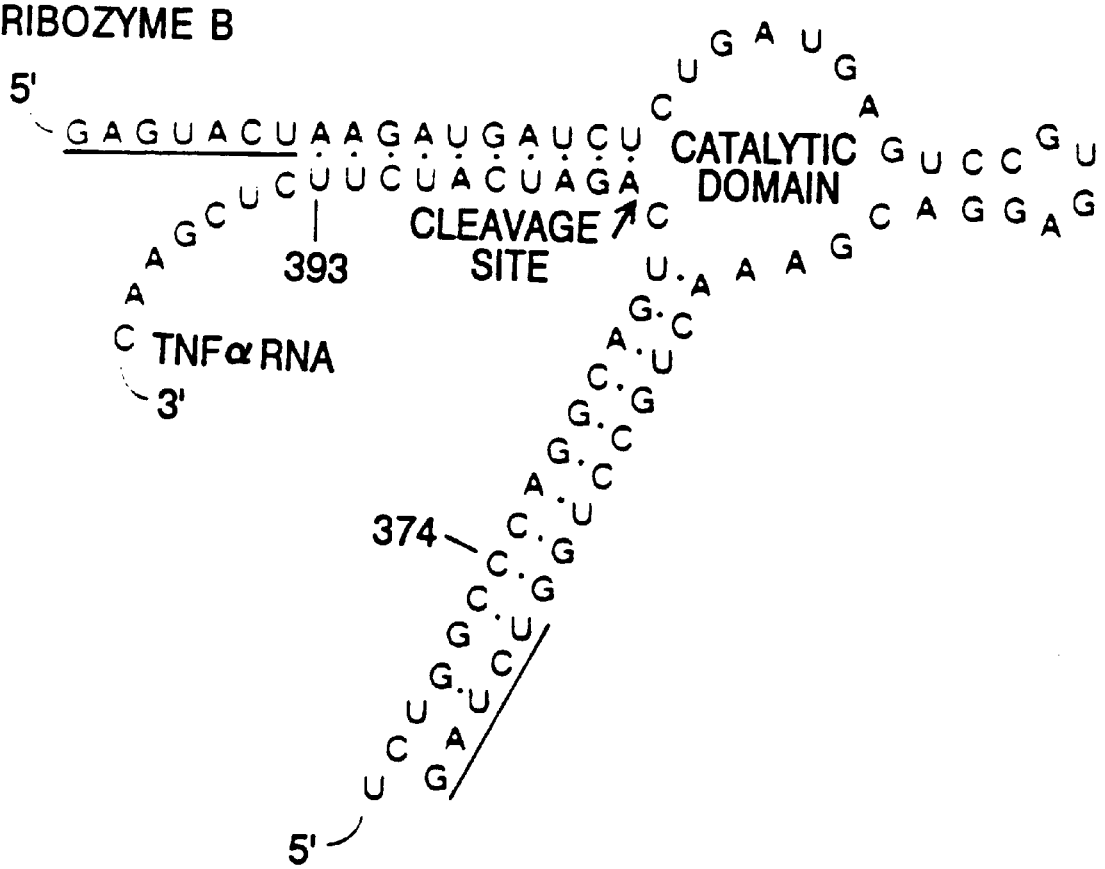
Figure 1C:
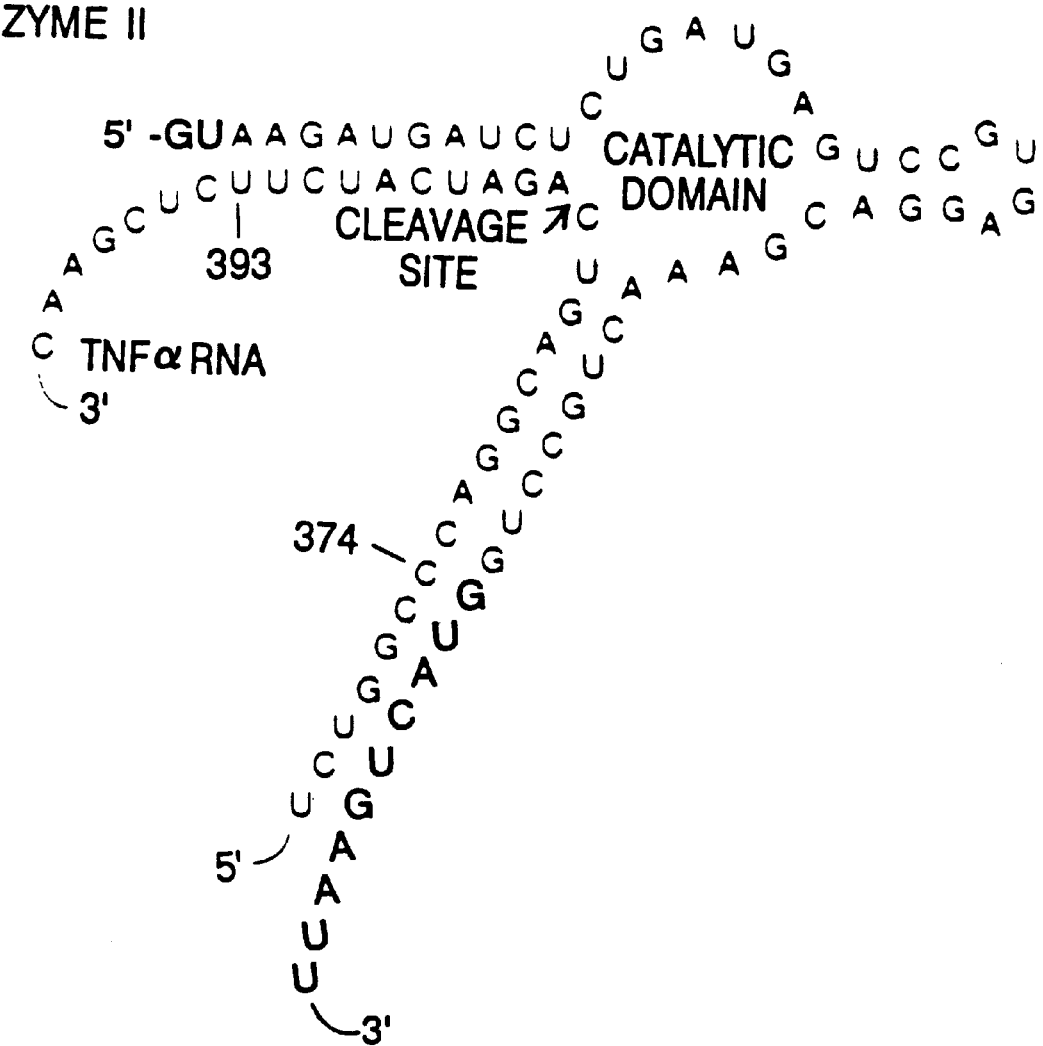

Three hammerhead ribozymes (Haseloff & Gerlach, 1988) designed to cleave the TNF-α RNA are shown in FIG. 1. Their in vitro activities were studied using total RNA extracted from PBMNC following stimulation of TNF-α gene transcription by phorbol 12-myristate 13-acetate (PMA) and concanavalin A (Con A) as described by English et al. (1991). Ribozyme A contained a bacteriophage T7 terminator at its 3' end while ribozyme B did not. Ribozyme II lacked the underlined restriction sites. FIG. 2 shows Ribozyme-mediated RNA cleavage assayed by gel electrophoresis and Northern blot hybridization using TNF-α probe. The TNF-α ribozyme cleaved the approximately 1800 nucleotide-long target RNA into fragments of 1420 and 380 nucleotides. The sizes of the TNF-α fragments produced by the ribozymes were consistent with the location of the predicted site for cleavage. Thus, ribozymes A and B cleave the TNF-α target in vitro in the presence of unrelated RNAs.

Stability of ribozymes A, B, and II in living cells

Stability of ribozyme A, B and II in living cells is shown in FIGS. 3 and 4. Since the cell membrane presents a substantial barrier to the entry of highly charged, high molecular weight molecules, delivering them to the cytoplasm is a major task. To overcome this, transfection techniques such as cationic liposome-mediated transfection (Malone et al., (1989) Proc. Natl. Acad. Sci., USA 86:6077–6081), electroporation (Callis et al., (1987) Nucl. Acids. Res. 15:5823–5831) and microinjection (Rosa et al., (1989) J. Cell. Biol. 109:17–34) have been developed. Since the liposome-based method appears to be the most versatile, its ability was tested to deliver enough functional ribozyme to successfully cleave TNF-α RNA.

The efficiency of RNA transfection was first measured in HL60 cells, as determined by measurement of cell-associated intact $^{32}$P-labelled RNA. Following transfection with ribozymes, cells were washed with Hank's buffered salt solution (GIBCO). Total RNA was prepared from cells and the RNA species were separated by gel electrophoresis. The radioactivity contained in the ribozyme RNA bands was then determined. The results indicate that the radioactive bands varied from 2 to 4% of the initial RNA added to the liposomes during the transfection period of between 8 and 20 hours. This corresponds to a delivery of approximately 300,000 molecules of ribozyme A per cell.

FIG. 4 shows stability of ribozymes A, B, and II. Ten million human HL60 cells (ATCC CCL 240), growing in log phase in RPMI 1640 supplemented with 20% (v/v) fetal calf serum (FCS), were used for RNA transfection. Cells were washed twice with serum-free medium. A drop (5 ml) of serum free medium was added to polystyrene tubes followed by 35 μg of lipofectin (Bethesda Research Laboratories), 10 μg of carrier RNA (*E. coli*. tRNA), and 3×10$^6$ disints min of $^{32}$p-labelled capped ribozyme A, B or II (5 μg). The mixture was immediately mixed. The cells were resuspended in a mixture of serum-free medium lipofectin/RNA/carrier RNA and returned to the incubator for 20 h. Following transfection the cells were washed 3 times with Hank's buffered saline solution and then returned to the incubator with RPMI supplemented with 20% FCS. Cells ($10^6$) were harvested at the times indicated above each lane, and total RNA was prepared and analyzed by 15% polyacrylamide gel with 7M-urea. The RNA samples used for transfection are indicated at the top of FIG. 4. A sample (50 µM) of labelled, capped ribozyme A was used to transfect HL60 cells for 20 h. Cells were washed 3 times, and the nuclear and cytoplasmic RNAs were prepared and analyzed by gel electrophoresis. For preparation of cytoplasmic and nuclear fractions, the cells were homogenized in 10 mM-Tris-HCl (pH 7·5). 5 mM-KCl, 140 mM-NaCl, 5 mM-dithiothreitol and 0.4% (w/v) Nonidet P40 for 10 min at 4° C. and the nuclei were collected by centrifugation at 800 g for 5 min. RNA in the supernatant was precipitated and saved as the cytoplasmic fraction. The nuclei were processed as described by Chomezynski & Sacchi (Anal. Biochem (1987) 162:156–160) for total RNA preparation. The arrow indicated the position of a ribozyme A monomer. The amount of radioactivity in the ribozyme bands shown in (a) was determined and expressed as a percentage of the radioactivity present immediately after 20 h transfection time.

FIG. 5 shows activity of Ribozymes in vivo Ribozymes and antisense RNA activities in HL60 cells (a) were analyzed after a transfection period (20 h). Following transfection with ribozyme A or antisense RNA, cells were stimulated for 6 h to express TNF-α. RNA was extracted, separated by gel electrophoresis using a 1–2% (w/v) agarose formaldehyde gel, and detected by Northern blotting with a radioactive probe for the TNF-α gene. Following hybridization with the TNF-α probe, the filter was stripped and then hybridized with an actin probe (British Biotechnology Limited). In the case of PBMNC (b) cells were separated (Sioud et al., Scand. J. Immunol. (1990 31:415–421) and washed 4 times with Hank's buffered saline solution and 3 times with serum-free medium. Cells ($10^6$) were transfected and processed as HL60 cells. Lanes 1 and 4, controls (transfected only with carrier RNA); lane 2, antisense RNA; lanes 3 and 5, ribozyme A. This auto-radiogram was overexposed to display the TNF-α signal in ribozyme A lanes. Radioinmunoassay for TNF-α protein (c). The amount of TNF-α protein present in the media was determined using the TNF-α [$^{125}$I] assay system (Amersham). Lanes 1 to 5 correspond to lanes 1 to 5 in FIG. 5(a) and (b), respectively.

Destruction of endogenous TNF-α RNA in vivo by ribozymes

Experiments were performed to determine if ribozyme A could eliminate its target following RNA transfection. A preliminary time-course study of TNF-α RNA synthesis in HL60 cells indicated that TNF-α RNA could be detected after two hours of stimulation by PMA and ConA, reaching maximal expression after four to six hours. Cells were transfected with ribozymes, stimulated with PMA and ConA for six hours, and total RNA was extracted and analyzed by Northern blotting using a TNF-α probe. Since the TNF-α and actin mRNA have approximately the same electrophoretic mobility, the same blot was hybridized with the actin probe after stripping. Data derived from densitometric scans of underexposed film indicated that the TNF-α signal was reduced by 40% (FIG. 5(a), antisense lane) and 90% (FIG. 3(a), ribozyme A lane). In addition, a radioimmunoassay was used to measure TNF-α protein in the culture medium. This system has major advantages over bio-assays in that it is specific for TNF-α. The data indicates that HL60 stimulated with PMA and ConA secrete as much as 1000 fmol of TNF-α per ml but only 150 and 400 when cells are transfected with ribozyme A and antisense, respectively (FIG. 5(b)).

Since the effect of antisense RNA is less than that of ribozyme A and since both ribozyme A and the antisense RNA were present inside the cells at similar concentrations (data not shown), we suggest that part of the activity of ribozyme A is due to its ability to cleave RNA. Ribozyme-mediated RNA cleavage in vivo has been observed in eukaryotic cells (Saxena & Ackerman, J. Biol. Chem. (1990) 265:17106–17109).

In this case, no cleavage products were seen. As suggested previously (Cotten & Birnstiel, 1989; Sarver et al., 1990; Sioud & Drlica, 1991) the products of ribozyme-mediated cleavage are probably degraded by cellular nucleases (the 5' fragment, although capped at its 5' end, is expected to be rapidly degraded by 3'→15' exonucleases).

The same conditions were used to deliver ribozyme A to PBMNC. As can be seen from FIG. 5(a) and (b), ribozyme A reduced the amount of TNF-α RNA by 80% and the TNF-α protein by 70% raising the possibility that liposome-mediated RNA transfection offers a way to deliver ribozymes to a wide variety of cell types. During analysis, ribozyme B appears to induce a similar reduction in TNF-α mRNA as ribozyme A (data not shown). Thus, the addition of T7 transcription terminator may decrease the specific activity of ribozyme A.

FIG. 6 shows cellular distribution of TNF-α ribozymes

The TNF-α ribozymes (FIG. 1) were unusually stable. They could be detected inside human cells for seven days, while normally, the ribozymes are unstable in human cells see FIG. 4. Although a cell fractionation study indicated that TNF-α ribozymes can be recovered from the cell, it did not address the possibility that a major portion of the ribozyme was sequestered in places inaccessible to cellular nucleases. To address this question cells were transfected with Digoxigenin labelled ribozymes. After 72 hours post transfection microscope slides were prepared and then the ribozyme were detected by anti-Digoxigen-fluoreceinFab conjugate as describe in materials and methods. Data present in FIGS. 5 A and B indicated that the stabilization effect was not due to any cellular compartmentalization, because upon immunofluorescence staining of the ribozyme, the whole cell acquired the fluorescence. See FIG. 6(a) and FIG. 6(B).

FIG. 7 shows electrophoretic mobility shift analysis of TNF-α ribozymes with cellular extracts.

The initial hypothesis was that the ribozyme directed against this particular site of tumor necrosis factor was protected by certain cellular factors such as proteins. If proteins were binding to the ribozyme and protecting it from degradation, mobility shift experiments should detect them. During initial experiments, carried out with HL60 cells cytoplasmic proteins revealed that the complexes formed were not inhibited by the presence of polydc dI and the tRNA in the reaction mixture. In these experiments there was still considerable degradation of the ribozyme due to the nucleases present in the extract. When RNAsin was then added to incubation mixture to lower the effect of ribonuclease a much greater portion of the input RNA was captured in the major complex (FIG. 7b lanes 2, 3 and 4). When, cytoplasmic extracts from PBMN cells were used, the complex with low electrophoretic mobility was also detectable (FIG. 7b lanes 6, 7), suggesting that the protein that binds to the ribozyme is a common protein to all cell types. The complexes formed in the presence or absence of RNasin had identical mobilities indicating that the proteins bind to the full length. Furthermore, the ribozyme recovered from the complex following phenol extraction corresponds to the full length ribozyme (FIG. 7b lane 8).

Complex formation is specific for TNF-α ribozymes

Adding tRNA to the reaction did not diminish the amount of complex formed, suggesting some specific binding to the ribozyme. This specificity of binding was confirmed by the competition assays (FIG. 8). In contrast to tRNA and Pol dCdI, unlabelled ribozyme competes with labelled ribozyme for complex formation. Interestingly complex formation was not observed with hammerhead ribozymes directed at mRNA of IL-2 or integrase of HIV. This indicates that the binding was not due to the catalytic domain of TNF-α ribozymes. Unlike the TNF-α the IL-2 ribozyme was not stable inside the cells as TNF-α ribozyme and does not exhibit this binding phenomenon. Thus, it is possible that this binding is responsible for the in vivo stability of the TNF-α ribozymes.

TNF-α ribozyme confers stability to other ribozymes

Even before characterizing this RNA element(s) that protects the TNF-α from degradation the possibility was tested that it could be tagged to other RNAs and stabilize them. The TNF-α ribozyme was linked to the IL-2 ribozyme (FIG. 9) which was unstable alone. As shown in FIGS. 10A and B, the IL-2 ribozyme alone did not form complexes on its own with any cellular factor in our conditions. As will be shown below, the TNF-α ribozyme linked to the IL-2 ribozyme did form complexes and was stabilized.

The in vivo activity of protected and unprotected IL-2 ribozymes.

We know that the inhibition of TNF-α gene expression by antisense or the ribozyme does not significantly effect the IL-2 gene expression. So the effect of the double ribozyme (IL-2 ribozyme linked to TNF-α ribozyme) on IL-2 gene expression could be investigated precisely.

The ribozyme directed against TNF-α ribozyme was protected by certain cellular factors such as proteins. These factor(s) could enhance the stability and/or activity of the ribozyme beyond structural stabilization. Such factor(s) or related compounds could be combined with the ribozyme by means of gene therapy approach.

Mobility shift experiments have been used to demonstrate successfully that protein(s) do bind to the TNF-α ribozyme (see FIGS. 8, 7 and 9). Pretreatment of the complex with proteinase K prior to electrophoresis eliminates the complex (FIG. 11 A, lanes 4 and 5) confirming that the cofactor is of a protein nature. The degradation of the ribozyme seen in lane 4 is due to the excess of ribonucleases present in this particular cytoplasmic extract (CE). Furthermore UV crosslinking analysis of proteins binding to the TNF-α ribozyme revealed a major ribozyme binding protein as can be seen from FIG. 11C: lane 1.

Similar complex formation was not observed with an integrase ribozyme, thus the protein is specific for TNF-α ribozyme and suggests that the difference in in vivo stability between the integrase ribozyme and TNF-α ribozyme may be due to the protein(s).

To see whether the linkage of TNF-α ribozyme to other RNA molecules conferred the protein binding and the in vitro and in vivo stability, the following minigenes were constructed:

1) IL-2 ribozyme linked to 5' of TNF-α ribozyme.

Since the TNF-α ribozyme and the integrase or IL-2 ribozyme differ only in the nucleotide sequence complementary to their RNA target, that RNA region is likely to be responsible for the complex formation.

2) IL-2 ribozyme linked to the antisense TNF-α RNA (see FIG. 9)

The genes coding for these molecules were cloned, in vitro transcribed and the radiolabelled RNA molecules were used in gel retardation assays.

Although weak complexes have been detected in some experiments, our data indicate that neither IL-2 linked to the 5' of TNF-α ribozyme nor the IL-2 ribozyme linked to the antisense bind to protein (For structure see FIG. 9). (FIG. 12A: lanes 4, 5, 7 and 8 and FIG. 12B: lanes 2 and 3). As can be seen from FIG. 12A, degradation of the IL-2 ribozyme and the chimeric molecules in the presence of CB was seen in all the lanes, indicating that the complex formation protects the ribozyme against degradation.

This data suggests that the binding of the protein requires a secondary structure. Since the T7 terminator linked at the 3' end of the TNF-α ribozyme did not affect the binding, it was thought that the ribozyme binding site could be formed between the 5' flanking sequence of TNF-α ribozyme and its catalytic domain. In addition, attempts were made to mimic the secondary structure of TNF-α ribozyme linked to T7 terminator (FIG. 13A).

TNF-α Antisense linked to 3' end of TNF-α ribozyme

The 3' end of the TNF-α ribozyme to an antisense directed against a different target on the TNF-α (FIG. 13B). The chosen antisense has a hairpin structure (keesing loop). Both genes were cloned, in vitro transcribed and then the radiolabelled RNA molecules were used in gel retardation assays.

The results (FIG. 14A: lanes 5 and 6) indicated that the antisense linked to 3' end of TNF-α ribozyme binds to protein(s). In addition competition experiments demonstrated that the same protein(s) are responsible for the complex formation, since unlabelled TNF-α ribozyme competed with the chimeric ribozyme for complex formation (FIG. 14B: lanes 3 and 4).

In the second experiments the IL-2 ribozyme was linked to the 3' end of TNF-α ribozyme (FIG. 15B). The flanking sequences of IL-2 ribozyme was extended in the construct in order to prevent intramolecular interaction.

The RNA generated from this chimeric ribozyme binds to protein(s) as TNF-α ribozyme (FIG. 16: lane 4). These experimental data suggest that the 5' flanking sequence of TNF-α ribozyme is involved in the binding.

Truncated TNF-α Ribozymes

To test the involvement of the flanking sequences, TNF-α ribozymes truncated at its 5' or 3' flanking sequence (FIG. 17A and 17B, respectively) were constructed.

The genes coding for these ribozymes were cloned, in vitro transcribed, and the radioactive RNA molecules were used in gel retardation assays. As can be seen from FIG. 18A lane 4, the 3' end truncated ribozyme binds to proteins. In contrast the 5' truncated TNF-α ribozyme does not form protein complex (FIG. 18A: lane 6). The band indicated by 0 is probably due to the intramolecular conformation of the ribozyme.

Gel retardation assays were used in order to see whether the 3' end truncated ribozyme binds to proteins from other cell types. As can be seen from FIG. 18D: lanes 2,3, and 4, the truncated ribozymes do bind to proteins from PBMN, HL60 and WH164 cells. Taken together our experimental data indicate that endogenous proteins from many cell types bind to the 3' truncated TNF-α ribozyme. Thus the capacity of any ribozyme to bind to protein(s) will depend on its 5' and perhaps 3' base composition.

A possible secondary structure for the TNF-α ribozyme B and II and the putative binding site of the protein are proposed in FIG. 19.

During this analysis, it was observed that in vitro complex formation protects the ribozyme against degradation (see FIG. 21A). Endogenous protein could be responsible for the unexpected stability of TNF-α ribozymes. Furthermore such endogenous protein(s) may enhance in vivo the ribozyme activity by helping to prevent and resolve misfolded ribozymes.

In vivo stability of IL-2, and IL-2 linked to 3' end of TNF-α ribozyme.

The stability of IL-2 ribozyme and the IL-2 ribozyme linked to 3' end of TNF-α ribozyme were investigated as previously reported. Briefly, HL60 cells growing in log phase in RPMI supplemented with 20% fetal calf sera were transfected with IL-2 ribozyme or IL-2 linked to TNF-α using DOTAP as transfection agent. Following transfection, cells were washed 3 times with Hank's buffered saline solution then returned to the incubator with RPMI supplemented with 20% FCS. Cells contained in 1 ml culture were harvested at different times. Total RNA was prepared and analyzed by 15% polyacrylamide gel with 7M urea. The radioactivity in ribozyme bands was determined and expressed as a percentage of the radioactivity present immediately after transfection time (FIG. 20). The data indicate that the chimeric ribozyme is more stable than the IL-2 ribozyme alone.

In vivo activity and cytotoxicity TNF-α ribozyme and TNF-α antisense linked to TNF-α ribozyme:

The in vivo activity of TNF-α ribozyme, the antisense and the antisense linked to TNF-α ribozyme was investigated using the cytotoxicity assay and radioimmunoassay. In these experiments the cellular internalization of the ribozymes was done by cationic liposome (DOTAP). A 36 nt long antisense complementary to the TNF-α sequence ranging from 56 to 91 (see Pennica et al., 1984, Nature 312:724) for numbering was linked to TNF-α ribozyme.

Approximately 100,000 PBMN cells were transfected with the ribozyme for 6 hrs or 12 hrs. The expression of TNF-α was induced with 10 μg of PHA for 16 hrs, and the secreted TNF-α in the media was measured by cytotoxicity assay using L929 cells. TNF-α inhibits growth of L929 cells. A high radioactive count (high level of incorporated 3H-thymidine) indicates a low level of TNF-α and hence effective ribozymes in PBMN cells. The level of TNF-α is considerably reduced when the peripheral blood is transfected with ribozymes. In addition, a radioimmunoassay was used to measure TNF-α in the culture medium. This system has a major advantage over bioassay in that it is specific for TNF-α.

The data presented in FIG. 21 indicate that all molecules are in vivo active. As may be expected, the antisense linked to the TNF-α ribozyme has a synergic effect.

One of the major problems when designing treatment is specificity and cytotoxicity. Thus the effects of TNF-α ribozyme and the TNF-α antisense linked to TNF-α ribozyme were investigated on interleukin 2 gene expression to check the specificity and cytotoxicity.

The molecules were delivered to the cells by cationic liposomes. Approximately 100,000 peripheral blood mononuclear cells were transfected with the test molecules for 5 hours. Following transfection, the cells were stimulated with 5 μg/ml PHA for 16 hours and then the quantity of interleukin 2 secreted in the media is determined using the CTLL2 assay. In this assay, a series of dilutions (¼ to ¹⁄₁₂₈) are made from the supernatant obtained from the controls and from cells transfected with the test molecules. 100 μl from each dilution (done in triplicates) are added to 5,000 CTLL2 cells in 20 μl medium. After 20 hours the cells are pulsed with 3H-thymidine for 4 hours, harvested, and then the DNA-associated radioactivity is determined. Interleukin-2 promotes the growth of CTLL2 cells, and so a high radioactive count indicates high levels of IL-2, and hence an ineffective ribozyme in PBMN cells.

FIG. 22 demonstrates that the expression of interleukin 2 is not effected by the TNF-α ribozyme. It also indicates that the ribozyme is not cytotoxic to the cells and that the IL-2 gene expression is not regulated by the level of TNF-α gene expression.

In vivo activity of IL-2 ribozyme and the IL-2 ribozyme linked to the 3' end of TNF-α ribozyme were investigated by CTLL2 assay.

Approximately 100,000 PBMN cells were transfected with the different molecules (25 μM final concentration) using DOTAP as cationic liposome. After 8 hrs of transfection the cells were stimulated with PHA (5 μg/ml) for 16 hrs and then the IL-2 in the media was assayed by the CTLL2 assay as shown in FIG. 22.

The data presented in FIG. 23 indicate that both ribozymes are active. The activity of IL-2 ribozyme linked to the 3' of TNF-α ribozyme is much higher than the IL-2 alone, suggesting that the protein may enhance both the stability and the activity of the ribozyme.

Another way to measure interleukin 2 gene expression is to pulse the PBMN cells directly with 3H-thymidine.

Following transfection the cells were stimulated with PHA for 48 hrs, pulsed with 3H-thymidine and then harvested 18 hrs later. In this assay IL-2 promotes the growth of T cells, and a high radioactive count indicates a high level of IL-2, and hence an ineffective molecule. The results of 3 experiments are presented below.

|  | A | B | C | D |
|---|---|---|---|---|
| exp1: | 2478 | 1566 | 566 | 130 |
| exp2 | 4641 | 1862 | 2000 | 213 |
| exp3 | 11403 | 5285 | 3586 | 32 |
| Medium | 6174 | 2904 | 2050 | 125 |
| % of inhibition | 0 | 53 | 67 | 0 |

A: Control
B: cells transfected with IL-2 ribozyme alone
C: cells transfected with IL-2 ribozyme linked to 3' end of TNF ribozyme
D: unstimulated cells The results presented in the above table indicate that both ribozymes are active in vivo. The IL-2 ribozyme linked to TNF-α ribozyme is more active than the IL-2 alone.

It has been demonstrated above that the 3' truncated ribozyme binds to proteins as TNF-α ribozyme. Thus this truncated ribozyme could be used as a stabilizer through the protein(s). In addition this truncated ribozyme will not be active, since it lacks its 3' end flanking sequences.

The in vivo activity of TNF-α ribozyme and the 3' truncated ribozyme was investigated at various transfection times, see below. As above, cells were transfected with the TNF-α ribozyme or the 3' truncated ribozyme using DOTAP. In these experiments the cells were stimulated with LPS (100 mg/ml) after 6, 20, 42 or 72 hrs post transfection time. The TNF-α contained in the media were measured by radioimmunoassay as described in the kit (Amerham). These data are expressed in fmol/ml.

| Hrs post transfection time | Cells transfected by 3' truncated ribozyme | Cells transfected by TNFα ribozyme | unst. cells |
|---|---|---|---|
| 6 | 284 | 180 | 24 |
| 20 | 350 | 116 | 52 |
| 42 | 1250 | 370 | 1250 |
| 72 | 1250 | 430 | 1250 |

These data indicate that the truncated ribozyme is not active compared to the TNF-α ribozyme and demonstrate that the TNF-α ribozyme is active even 72 hrs post transfection time.

As can be seen after 42 hrs the unstimulated cells secreted the same amount of TNF-α as the controls which have been stimulated. This may be due to the fact that the cells have been stimulated through contact with the plastic (it is known that long exposure of the cells to plastic could stimulate the expression of some lymphokine genes). Thus, the decay of ribozyme activity seen 48 hrs post transfection time may be due to the overexpression of the TNF-α gene due to the long exposure to the plastic and/or the decay of the ribozyme itself.

CONCLUSIONS

Thus we have demonstrated that TNF-α ribozymes are unusually stable inside human cells. This phenomenon is not easily explained in terms of intracellular location, since the ribozyme appear to be distributed throughout the cells (FIG. 6). A significant fraction of the ribozyme was recovered as complex having reduced electrophoretic mobility. Suppression of the ribonucleases by RNAsin increases the recovery of the complexes from cytoplasmic extracts. Addition of tRNA had no competitive effect. Inhibition of complex formation was obtained with only unlabelled ribozyme. Neither integrase nor IL-2 ribozymes formed detectable complexes. Thus, the binding is specific for TNF-α ribozyme. The IL-2 ribozyme showed a reduced intracellular stability compared to the TNF-α ribozyme, raising the possibility that complexes formation is related to the stability.

The linkage of TNF-α ribozyme to IL-2 ribozyme both increased stability and conferred the ability to the double ribozyme to form complexes. Further, the linked ribozymes were active.

Thus, a 3' end truncated ribozyme binds to proteins. In contrast to 5' truncated TNF-α ribozyme does not form protein complex. Thus the capacity of any ribozyme to bind to protein(s) will depend on its 5' and perhaps 3' base composition including the length. Our data will help to design such ribozyme binding endogenous protein(s).

What is claimed is:

1. An RNA molecule having the structure (SEQ ID No:5):

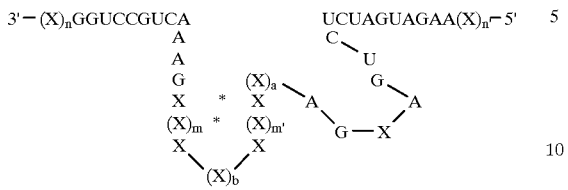

wherein each X represents a ribonucleotide which may be the same or different;

wherein each of $(X)_n$ and $(X)_{n'}$ represents an oligonucleotide having a predetermined sequence;

wherein each of n and n' represents an integer;

wherein each 0 represents base pairing between the ribonucleotides located on either side thereof;

wherein each solid line represents a chemical linkage providing covalent bonds between the ribonucleotides located on either side thereof;

wherein a represents an integer which defines a number of ribonucleotides with the proviso that a may be 0 or 1 and if 0, the A located 5' of $(X)_a$ is bonded to the X located 3' of $(X)_a$;

wherein each of m and m' represents an integer which is greater than or equal to 1;

wherein $(X)_b$ represents an oligoribonucleotide with the proviso that b represents an integer which is greater than or equal to 2.

2. The RNA molecule of claim 1, wherein at least one of $(X)_n$ or $(X)_{n'}$ comprises a ribozyme.

3. The RNA molecule of claim 2, wherein the ribozyme is a hairpin ribozyme.

4. The RNA molecule of claim 2, wherein the ribozyme is the RNA moiety of RNAse P.

5. The RNA molecule of claim 2, wherein the ribozyme is a hammerhead ribozyme.

6. The RNA molecule of claim 2, wherein the ribozyme is a hepatitis delta ribozyme.

7. The RNA molecule of claim 2, wherein $(X)_n$ or $(X)_{n'}$ has the structure (SEQ ID NO: 8):

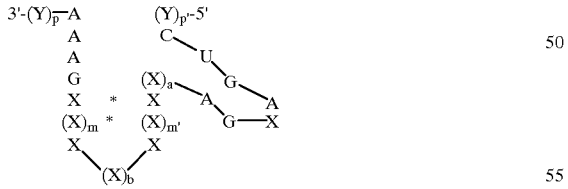

wherein each of X and Y represents a ribonucleotide which may be the same or different;

wherein each of $(Y)_p$ and $(Y)_{p'}$ represents an oligonucleotide having a predetermined sequence which is capable of hybridizing with an RNA target sequence to be cleaved;

wherein each of p and p' represents an integer which defines the number of ribonucleotides in the oligonucleotide with the proviso that the sum of p+p' is sufficient to allow the ribozyme to hybridize with the RNA target sequence;

wherein each 0 represents base pairing between the ribonucleotides located on either side thereof;

wherein each solid line represents a chemical linkage providing covalent bonds between the ribonucleotides located on either side thereof;

wherein a represents an integer which defines a number of ribonucleotides with the proviso that a may be 0 or 1 and if 0, the A located 5' of $(X)_a$ is bonded to the X located 3' of $(X)_a$;

wherein each of m and m' represents an integer which is greater than or equal to 1;

wherein $(X)_b$ represents an oligoribonucleotide with the proviso that b represents an integer which is greater than or equal to 2.

8. The RNA molecule of claim 5, wherein $(X)_{n'}$ has the structure (SEQ ID NO: 8):

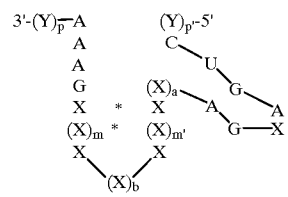

wherein each of X and Y represents a ribonucleotide which may be the same or different;

wherein each of $(Y)_p$ and $(Y)_{p'}$ represents an oligonucleotide having a predetermined sequence which is capable of hybridizing with an RNA target sequence to be cleaved;

wherein each of p and p' represents an integer which defines the number of ribonucleotides in the oligonucleotide with the proviso that the sum of p+p' is sufficient to allow the ribozyme to hybridize with the RNA target'sequence;

wherein each 0 represents base pairing between the ribonucleotides located on either side thereof;

wherein each solid line represents a chemical linkage providing covalent bonds between the ribonucleotides located on either side thereof;

wherein a represents an integer which defines a number of ribonucleotides with the proviso that a may be 0 or 1 and if 0, the A located 5' of $(X)_a$ is bonded to the G located 3' of $(X)_a$;

wherein each of m and m' represents an integer which is greater than or equal to 1;

wherein $(X)_b$ represents an oligoribonucleotide with the proviso that b represents an integer which is greater than or equal to 2.

9. The RNA molecule of claim 5, 7, or 8, having the structure (SEQ ID NO:9):

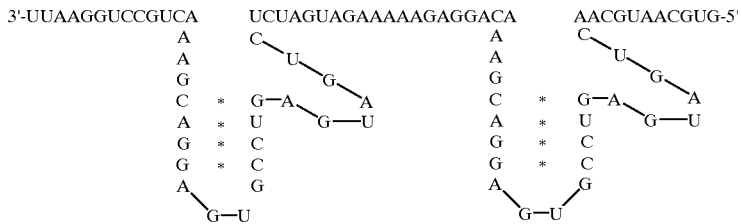

10. The RNA molecule of claim 5 or 7, having the structure (SEQ ID NO:14):

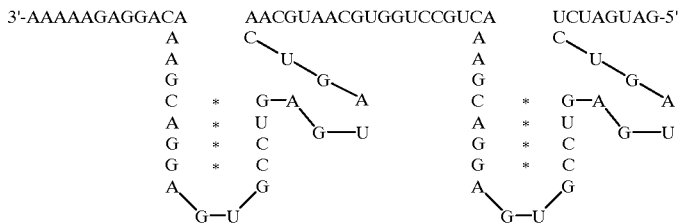

11. The RNA molecule of claim 1, wherein $(X)_n$ or $(X)_{n'}$ encodes a polypeptide.

12. The RNA molecule of claim 1, wherein $(X)_n$ or $(X)_{n'}$ is capable of hybridizing to an RNA indigenous to a mammal.

13. The RNA molecule of claim 1, wherein $(X)_n$ or $(X)_{n'}$ is capable of hybridizing to an RNA indigenous to a plant.

14. A method for producing the compound of claim 1, which comprises the steps of:

(a) ligating into a transfer vector comprised of DNA, RNA or a combination thereof a nucleotide sequence corresponding to said compound;

(b) transcribing the nucleotide sequence of step (a) with RNA polymerase; and (c) recovering the compound.

15. A prokaryotic or eukaryotic cell containing a nucleotide sequence which on transcription gives rise to the compound of claim 1.

16. The RNA molecule of claim 7 or 8, wherein $(X)_n$ or $(X)_{n'}$ has the structure (SEQ ID NO: 8):

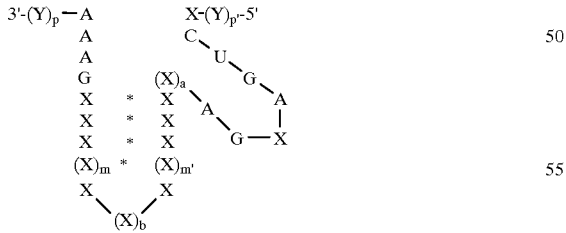

wherein each of X and Y represents a ribonucleotide which may be the same or different;

wherein each of $(Y)_p$ and $(Y)_{p'}$ represents an oligonucleotide having a predetermined sequence which is capable of hybridizing with an RNA target sequence to be cleaved;

wherein each of p and p' represents an integer which defines the number of ribonucleotides in the oligonucleotide with the proviso that the sum of p+p' is sufficient to allow the ribozyme to hybridize with the RNA target sequence;

wherein each 0 represents base pairing between the ribonucleotides located on either side thereof;

wherein each solid line represents a chemical linkage providing covalent bonds between the ribonucleotides located on either side thereof;

wherein a represents an integer which defines a number of ribonucleotides with the proviso that a may be 0 or 1 and if 0, the A located 5' of $(X)_a$ is bonded to the X located 3' of $(X)_a$;

wherein each of m and m' represents an integer which is greater than or equal to 1;

wherein $(X)_b$ represents an oligoribonucleotide with the proviso that b represents an integer which is greater than or equal to 2.

17. The RNA molecule of claim 7 or 8, wherein $(X)_{n'}$ has the structure (SEQ ID NO:8):

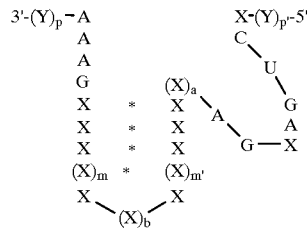

wherein each of X and Y represents a ribonucleotide which may be the same or different;

wherein each of $(Y)_p$ and $(Y)_{p'}$ represents an oligonucleotide having a predetermined sequence, which is capable of hybridizing with an RNA target sequence to be cleaved;

wherein each of p and p' represents an integer which defines the number of ribonucleotides in the oligonucleotide with the proviso that the sum of p+p' is sufficient to allow the ribozyme to hybridize with the RNA target sequence;

wherein each represents base pairing between the ribonucleotides located on either side thereof;

wherein each solid line represents a chemical linkage providing covalent bonds between the ribonucleotides located on either side thereof;

wherein a represents an integer which defines a number of ribonucleotides with the proviso that a may be 0 or 1 and if 0, the A located 5' of $(X)_a$ is bonded to the X located 3' of $(X)_a$;

wherein each of m and m' represents an integer which is greater than or equal to 1;

wherein $(X)_b$ represents an oligoribonucleotide with tne proviso that b represents an integer which is greater than or equal to 2.

18. The RNA molecule of claim 16, wherein $(X)_n$ or $(X)_{n'}$ encodes a polypeptide.

19. The RNA molecule of claim 16, wherein $(X)_n$ or $(X)_{n'}$ is capable of hybridizing to an RNA indigenous to a mammal.

20. The RNA molecule of claim 16, wherein $(X)_n$ or $(X)_{n'}$ is capable of hybridizing to an RNA indigenous to a plant.

21. A method for producing the compound of claim 16, which comprises the steps of:

(a) ligating into a transfer vector comprised of DNA, RNA or a combination thereof a nucleotide sequence corresponding to said compound;

(b) transcribing the nucleotide sequence of step (a) with RNA polymerase; and (c) recovering the compound.

22. A transfer vector which comprises RNA or DNA or a combination thereof containing a nucleotide sequence which on transcription gives rise to the compound of claim 16.

23. A transfer vector according to claim 22 which comprises RNA or DNA or a combination thereof derived from a bacterial plasmid or a phage.

24. A prokaryotic or eukaryotic cell containing a nucleotide sequence which on transcription gives rise to the compound of claim 16.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: Other nucleic acid
      (A) DESCRIPTION: (Mixed DNA/RNA oligomer
          see specification and figures for details)

(xi) SEQUENCE DESCRIPTION: SEQ ID NO:1:

NAAGAUGAUC UCUGANGANN NNNNNNNNNN GAAACUGCCU GGN      43

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: Other nucleic acid
      (A) DESCRIPTION: (Mixed DNA/RNA oligomer
          see specification and figures for details)

(xi) SEQUENCE DESCRIPTION: SEQ ID NO:2:

AAGAUCUACU GCCUGG      16

(2) INFORMATION FOR SEQ ID NO:3:

```
    (i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
              see specification and figures for details)

(xi) SEQUENCE DESCRIPTION: SEQ ID NO:3:

AAGAUGAUCU CUGAUGANNN NNNNNNNNNG AAACUGCCUG GN                           42

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:4:

AAGAUGAUCU CUGAUGAGUC CGUGAGGACG AAACUGCCUG GN                           42

(2) INFORMATION FOR SEQ ID NO:5:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
              see specification and figures for details)

(xi) SEQUENCE DESCRIPTION: SEQ ID NO:5:

NAAGAUGAUC UCUGANGANN NNNNNNNNNN GAAACUGCCU GGN                          43

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:6:

NAAGAUGAUC UGACUGCCUG GN                                                 22

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:7:

AAGAUGAUCU ACUGCCUGG                                                     19

(2) INFORMATION FOR SEQ ID NO:8:

(i) SEQUENCE CHARACTERISTICS:
```

```
        (A) LENGTH: 26 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:8:

NNCUGANGAN NNNNNNNNNN NGAAAN                                              26

(2) INFORMATION FOR SEQ ID NO:9:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:9:

GUGCAAUGCA ACUGAUGAGU CCGUGAGGAC GAAACAGGAG AAAAAGAUGA UCUCUGAUGA         60

GUCCGUGGGG ACGAAACUGC CUGGAAUU                                           88

(2) INFORMATION FOR SEQ ID NO:10:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:10:

GAAAUGAUCU CUGAUGAGUC CGUGAGGACG AAACUGCCUG GAAAUGCAAU GCAACUGAUG         60

AGUCCGUGAG GACGAAACAG GAGAAUU                                            87

(2) INFORMATION FOR SEQ ID NO:11:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:11:

GGUGCAAUGC AACUGAUGAG UCCGUGAGGA CGAAACAGGA GAAUUGAUGA UCUGACUGCC         60

UGGAAUU                                                                  67

(2) INFORMATION FOR SEQ ID NO:12:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:12:

GGAUGAUCUG ACUGCCUGGA AUUGUGCAAU GCAACUGAUG AGUCCGUGAG GACGAAACAG         60

GAGAAUU                                                                  67
```

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:13:

```
NNCUGANGAN GAAAN                                              15
```

(2) INFORMATION FOR SEQ ID NO:14:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:14:

```
GAUGAUCUCU GAUGAGUCCG UGAGGACGAA ACUGCCUGGU GCAAUGCAAC UGAUGAGUCC    60

GUGAGGACGA AACAGGAGAA AAA                                            83
```

(2) INFORMATION FOR SEQ ID NO:15:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:15:

```
GAGUACUAAG AUGAUCUCUG AUGAGUCCGU GAGGACGAAA CUGCCUGGUC UAGACAUAAC    60

CCCUUGGGGC CUCUAAACGG GUCUUGAGGG UUUUUUC                             97
```

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:16:

```
UCUGGCCCAG GCAGUCAGAU CAUCUUCUCG AAC                          33
```

(2) INFORMATION FOR SEQ ID NO:17:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:17:

```
GAGUACUAAG AUGAUCUCUG AUGAGUCCGU GAGGACGAAA CUGCCUGGUC UAG     53
```

(2) INFORMATION FOR SEQ ID NO:18:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: RNA (genomic)

(xi) SEQUENCE DESCRIPTION: SEQ ID NO:18:

GUAAGAUGAU CUCUGAUGAG UCCGUGAGGA CGAAACUGCC UGAAUU           46

(2) INFORMATION FOR SEQ ID NO:19:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AACAGCTGTA ATACGACTCA CTATAGAGTA CTAAGATGAT CTCTGATGAG TCCGTGAGGA     60

CGAAACTGA                                                            69

(2) INFORMATION FOR SEQ ID NO:20:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TTCTCGAGAA AAAACCCTCA AGACCCGTTT AGAGGCCCCA AGGGGTTATG TCTAGACCAG     60

GCAGTTTCGT CC                                                        72

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AACAGCTGTA ATACGACTCA CTATAGAGTA CTAAGATGAT CTGACTGCCT GGTCTAG        57

(2) INFORMATION FOR SEQ ID NO:22:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTCTCGAGAA AAAACCCTCA AGACCCGTTT AGAGGCCCCA AGGGGTTATG TCTAGACCAG     60

CA                                                                   62

(2) INFORMATION FOR SEQ ID NO:23:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:23:

```
GGUGCAAUGC AACUGAUGAG UCCGUGAGGA CGAAACAGGA GAAUUNNNN            49
```

(2) INFORMATION FOR SEQ ID NO:24:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:24:

```
GGUGCAAUGC AACUGAUGAG UNCCGUNNNN GAGGACGAAA CANNGGAGAA AAGAUGAUC   60

UCUGAUGANN NGUCCGUGAG GACGAAACUC CNUGGAAUUN NNNNNN              106
```

(2) INFORMATION FOR SEQ ID NO:25:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:25:

```
GGUGCAAUGC AACUGAUGAG UCCGUGAGGA CGNAAACAGG AGUUAAGAUG AUCUGUUACU  60

GNCCUNNNGG AAUNNNNNNN NNNNNNNNNN                                  90
```

(2) INFORMATION FOR SEQ ID NO:26:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:26:

```
GUAAGAUGAU CUCUGAUGAG UCCGUGAGGA CGAAACUGCC UGGUACUAAC CCCUUGGGGC  60

CUCUAAACGG GUCUUGAGGG GUUUUUUGAA UU                                92
```

(2) INFORMATION FOR SEQ ID NO:27:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:27:

```
GUAAGAUGAU CUCUGAUGAG UCCGUGAGGA CGAAACUGCC UGGUACUGAA GGCCAGCUCC  60
```

```
ACGUCCCGGA UCAUGCUUUC AGUGCUCAUG AAUU                                   94

(2) INFORMATION FOR SEQ ID NO:28:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:28:

GACUUAGUGC AAUGCAACUG AUGAGUCCGU GAGGACGAAA CAGGAGUUGC GAAUU           55

(2) INFORMATION FOR SEQ ID NO:29:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:29:

GUAAGAUGAU CUCUGAUGAG UCCGUGAGGA CGAAACUGCC UGGUAUGAAA AAAGACUUAG       60

UGCAAUGCAA CUGAUGAGUC CGUGAGGACG AAACAGGAGU UGCGAAUU                  108

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:30:

GCUGAUGAGU CCGUGAGGAC GAAACUGCCU GGUACUAAAU U                           41

(2) INFORMATION FOR SEQ ID NO:31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:31:

GUAAGAUGAU CUCUGAUGAG UCCGUGAGGA CGAAGAAUU                              39

(2) INFORMATION FOR SEQ ID NO:32:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:32:

GAGUACUAAG AUGAUCUCUG AUGAGUCCGU GAGGACGAAA CUGCCUGGU                  49
```